US010610863B2

United States Patent
Lee et al.

(10) Patent No.: US 10,610,863 B2
(45) Date of Patent: Apr. 7, 2020

(54) AUTOMATIC MICROFLUIDIC SYSTEM FOR ANTIBIOTIC SUSCEPTIBILITY TESTING AND METHOD OF OPERATING THEREOF

(71) Applicants: NATIONAL TSING HUA UNIVERSITY, Hsinchu (TW); Kaohsiung Chang Gung Memorial Hospital, Kaohsiung (TW)

(72) Inventors: Gwo-Bin Lee, Hsinchu (TW); Shiuann-Sheng Lee, Taipei (TW); Wen-Bin Lee, Hsinchu (TW); Wen-Hsin Chang, Hsinchu (TW)

(73) Assignees: NATIONAL TSING HUA UNIVERSITY, Hsinchu (TW); Kaohsiung Chang Gung Memorial Hospital, Kaohsiung (TW)

( * ) Notice: Subject to any disclaimer, the term of this patent is extended or adjusted under 35 U.S.C. 154(b) by 180 days.

(21) Appl. No.: 15/582,781

(22) Filed: May 1, 2017

(65) Prior Publication Data

US 2018/0142279 A1   May 24, 2018

(30) Foreign Application Priority Data

Nov. 24, 2016   (TW) .............................. 105138682 A

(51) Int. Cl.
*B01L 3/00*   (2006.01)
*C12Q 1/04*   (2006.01)

(52) U.S. Cl.
CPC .......... *B01L 3/502738* (2013.01); *C12Q 1/04* (2013.01); *B01L 2300/0867* (2013.01);
(Continued)

(58) Field of Classification Search
CPC ......... B01L 3/502738; B01L 2300/123; B01L 2300/0867; B01L 2400/0655; B01L 2400/0487; C12Q 1/04
See application file for complete search history.

(56) References Cited

U.S. PATENT DOCUMENTS

| | | | | |
|---|---|---|---|---|
| 2005/0221281 A1* | 10/2005 | Ho | ......................... | B01L 3/5025 435/4 |
| 2013/0130232 A1* | 5/2013 | Weibel | ............. | G01N 33/54386 435/5 |
| 2015/0376684 A1* | 12/2015 | Lee | ......................... | C12Q 1/689 506/12 |

FOREIGN PATENT DOCUMENTS

TW   I324531 B   5/2010
TW   201600606 A   1/2016

OTHER PUBLICATIONS

Wen-Bin Lee et al. "A microfluidic device for antimicrobial susceptibility testing based on a broth dilution method". Biosensors and Bioelectronics. Jan. 15, 2017, vol. 87, pp. 669-678. (Year: 2017).*
(Continued)

*Primary Examiner* — Michael L Hobbs
(74) *Attorney, Agent, or Firm* — CKC & Partners Co., LLC

(57) ABSTRACT

An automatic microfluidic system for antibiotic susceptibility testing of the present disclosure at least includes a microfluidic chip. The microfluidic chip includes a fluid storage unit, a reaction unit, a pneumatic micro-pumping unit and a plurality of valve units. The fluid storage unit is provided for storing a bacterial suspension, a broth and an antibiotic solution. The reaction unit includes a first reaction chamber and at least two second reaction chambers. The pneumatic micro-pumping unit is adjacently disposed to the fluid storage unit and the reaction unit for selectively, repeatedly and quantitatively transporting the broth, the bacterial suspension and the antibiotic solution to the reaction unit to form a first mixing solution and at least two second mixing solutions. The valve units include a plurality of pneumatic micro-valves and a plurality of valve control air holes for controlling the opening and closing of the pneumatic micro-valves.

24 Claims, 12 Drawing Sheets
(3 of 12 Drawing Sheet(s) Filed in Color)

(52) U.S. Cl.
CPC . *B01L 2300/123* (2013.01); *B01L 2400/0487* (2013.01); *B01L 2400/0655* (2013.01)

(56) References Cited

OTHER PUBLICATIONS

Wen-Bin Lee et al., "A microfluidic device for antimicrobial susceptibility testing based on a broth dilution method", Biosensors and Bioelectronics, published on Jan. 15, 2017, vol. 87, pp. 669-678, published by Elsevier B.V., Netherlands.

Wen-Bin Lee et al., "A microfluidic device for minimum inhibitory concentration determination of antimicrobial susceptibility testing by using liquid broth dilutions" The 26th Anniversary World Congress on Biosensors (Biosensors 2016), dated on May 25-27, 2016, poster, Sweden.

Wen-Bin Lee et al., "A Microfluidic Device for Antimicrobial Susceptibility Testing of Combined Antibiotics by Using Broth Dilution Method", The 30th IEEE International Conference on Micro Electro Mechanical Systems (MEMS 2017), dated on Jan. 22-26, 2017, poster, United States.

Jing Dai et al., "Microfluidics for Antibiotic Susceptibility and Toxicity Testing", Bioengineering, published in Dec. 2016, pp. 1-13, vol. 3, issue 4, published by MDPI, Switzerland.

Wen-Hsin Chang et al., "Rapid isolation and diagnosis of live bacteria from human joint fluids by using an integrated microfluidic system", Lab on a Chip, published on Sep. 7, 2014, issue 17, vol. 14, pp. 3376-3384, published by Royal Society of Chemistry, United Kingdom.

\* cited by examiner

AUTOMATIC MICROFLUIDIC SYSTEM FOR ANTIBIOTIC SUSCEPTIBILITY TESTING AND METHOD OF OPERATING THEREOF

RELATED APPLICATIONS

This application claims priority to Taiwan Application Serial Number 105138682, filed Nov. 24, 2016, which is herein incorporated by reference.

BACKGROUND

Technical Field

The present disclosure relates to a microfluidic system. More particularly, the present disclosure relates to an automatic microfluidic system for antibiotic susceptibility testing and method for operating thereof.

Description of Related Art

Indiscriminate utilization of antibiotics in human medicine and animal husbandry in recent years has accelerated the selection process, leading to a rise in the number of antibiotic-resistant bacteria. A hospital-acquired infection (HAI), which is resulted from multiple antibiotic-resistant bacteria, has a high death rate. In addition, the consequent increase in difficulty in fighting bacterial infections has resulted in longer hospitalization periods and worse prognoses, both of which are associated with increases in medical expenses. That is, how to reduce probability of the hospital-acquired infection and use antibiotics correctly becomes an important issue recently.

Strains of vancomycin-resistant *Enterococcus* (VRE) are a common type of bacteria that has caused a large number of severe, hospital-acquired infections, and a ratio of the hospital-acquired infections caused by the strains of vancomycin-resistant *Enterococcus* are raised year by year. vancomycin-resistant genes of the strains of vancomycin-resistant *Enterococcus* can be transferred among several kinds of bacteria, however, it increases the difficulty of the clinical treatment. In order to improve the abovementioned situation, it needs to prevent each kind of infection paths and establish a complete monitoring system for the antibiotic-resistant bacteria. Moreover, a quickly and precious system for an antibiotic susceptibility testing is required for reducing occurrences of the antibiotic-resistant bacteria caused by a repeated dosing or a preventive dosing.

The current protocol for the antibiotic susceptibility testing involves first identifying the bacterial flora present by culturing bacteria isolated from patient specimens in liquid broth via disk diffusion on agar plates to measure the minimum dosage of an antibiotic that inhibits bacteria growth. Other protocols, such as minimum inhibitory concentration (MIC), minimum bactericidal concentration (MBC) and time-kill curves test, are also used. Furthermore, a gene sequence analysis is also applied for detecting the antibiotic-resistant bacteria recently and developed as a commercial kit.

However, the dosage of the antibiotic for the clinical treatment needs to be determined preciously, especially for the treatment of the antibiotic-resistant bacteria. Thus, a quantitative testing is required for assisting a doctor to determine a clinical dosage and avoiding an incorrect dosing. In particular, the antibiotic susceptibility testing is performed according to Clinical and Laboratory Standards Institute (hereafter referred as CLSI) guidelines. More particularly, bacteria or samples to be tested will be added into culture media with different concentrations of the antibiotic, separately. After incubation for 24 hours, a minimum inhibitory concentration can be determined. The less the minimum inhibitory concentration is, the stronger the antibiotic for the bacteria or samples is. The clinical result of applying the antibiotic, which is obtained in vitro, can assist the doctor to avoid the serious resistance caused by the repeating dosing. However, the abovementioned techniques are complicated, relatively labor-intensive and require a significant amount of training.

As the resistance of bacteria to drugs continues to increase whereas the discovery rate of new antibiotics declines, combinational antibiotics therapy has been frequently used to treat bacterial infections for clinicians and to prevent the prescription of ineffective antibiotics. A fractional inhibitory concentration (FIC) index is a commonly used formula to provide a quantitative estimate of the activities of two antibiotics in combination against antibiotics-resistant bacteria. The determination of the fractional inhibitory concentration index is conventionally performed by using a checkerboard microtiter plate method. In details, two antibiotics to be tested are diluted to different concentrations, separately, and loaded to each well of a 96-well plate. A bacterial suspension is then loaded to each well of the 96-well plate for incubation, and a combined inhibitory concentration is determined. The fractional inhibitory concentration index is calculated as the quotient between the combined inhibitory concentration and the minimum inhibitory concentration of each antibiotic. Finally, the combination of the two antibiotics will be considered as synergistic activity, additive activity, indifferent activity or antagonistic activity. However, it is also labor-intensive and time-consuming. Furthermore, human error and contamination are inevitable.

Accordingly, there is an urgent need to develop a precious and quick system for antibiotic susceptibility testing with low cost.

SUMMARY

The present disclosure provides an automatic microfluidic system for antibiotic susceptibility testing. The microfluidic system includes a microfluidic chip, and the microfluidic chip includes a fluid storage unit, a reaction unit, a pneumatic micro-pumping unit and a plurality of valve units. The fluid storage unit includes a first fluid storage chamber, a second fluid storage chamber and a third fluid storage chamber. The first fluid storage chamber is for storing a bacterial suspension, the second fluid storage chamber is for storing a broth, and the third fluid storage chamber is for storing an antibiotic solution. The reaction unit includes a first reaction chamber and at least two second reaction chambers. The pneumatic micro-pumping unit is adjacently disposed to the fluid storage unit and the reaction unit. The pneumatic micro-pumping unit is applied for repeatedly and quantitatively transporting the broth and the bacterial suspension to the first reaction chamber to form a first mixing solution and for repeatedly and quantitatively transporting the broth, the bacterial suspension and the antibiotic solution to the second reaction chambers to form at least two second mixing solutions. The valve units include a plurality of pneumatic micro-valves and a plurality of valve control air holes. The pneumatic micro-valves are disposed between the fluid storage unit and the pneumatic micro-pumping unit, and between the pneumatic micro-pumping unit and the reaction unit. The valve control air holes are for controlling the opening and closing of the pneumatic micro-valves.

The present disclosure further provides a method for operating one embodiment of the abovementioned automatic microfluidic system for antibiotic susceptibility testing. The method includes performing a first transportation step, performing at least one second transportation step, performing at least one third transportation step, performing an incubation step and performing a determination step. The first transportation step is performed for transporting the bacterial suspension to each of the first reaction chamber and the second reaction chambers by the pneumatic micro-pumping unit. The second transportation step is performed for transporting the broth to each of the first reaction chamber and the second reaction chambers by the pneumatic micro-pumping unit. The third transportation step is performed for transporting the antibiotic solution to at least one of the second reaction chambers by the pneumatic micro-pumping unit, in which a concentration of the antibiotic solution in each of the second mixing solutions is adjusted by a frequency of transporting the antibiotic solution and the broth to the second reaction chamber. In the incubation step, the first mixing solution and the second mixing solutions are allowed to stand for an incubation time. The determination step is performed for determining a result of the antibiotic susceptibility testing.

The present disclosure further provides a method for operating the other embodiment of the abovementioned automatic microfluidic system for antibiotic susceptibility testing. The method includes performing a first transportation step, performing at least one second transportation step, performing at least one third transportation step, performing an incubation step and performing a determination step. The first transportation step is performed for transporting the bacterial suspension to each of the first reaction chamber and the second reaction chambers by the pneumatic micro-pumping unit. The second transportation step is performed for transporting the broth to each of the first reaction chamber and the second reaction chambers by the pneumatic micro-pumping unit. The third transportation step is performed for transporting the antibiotic solution and the other antibiotic solution to at least one of the second reaction chambers by the pneumatic micro-pumping unit, in which concentrations of the antibiotic solution and the other antibiotic solution in each of the second mixing solutions is adjusted by a frequency of transporting the antibiotic solution, the other antibiotic solution and the broth to each of the second reaction chambers. In the incubation step, the first mixing solution and the second mixing solutions are allowed to stand for an incubation time. The determination step is performed for determining a result of the antibiotic susceptibility testing.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiments, with reference made to the accompanying drawings as follows.

DETAILED DESCRIPTION

Figure 1:
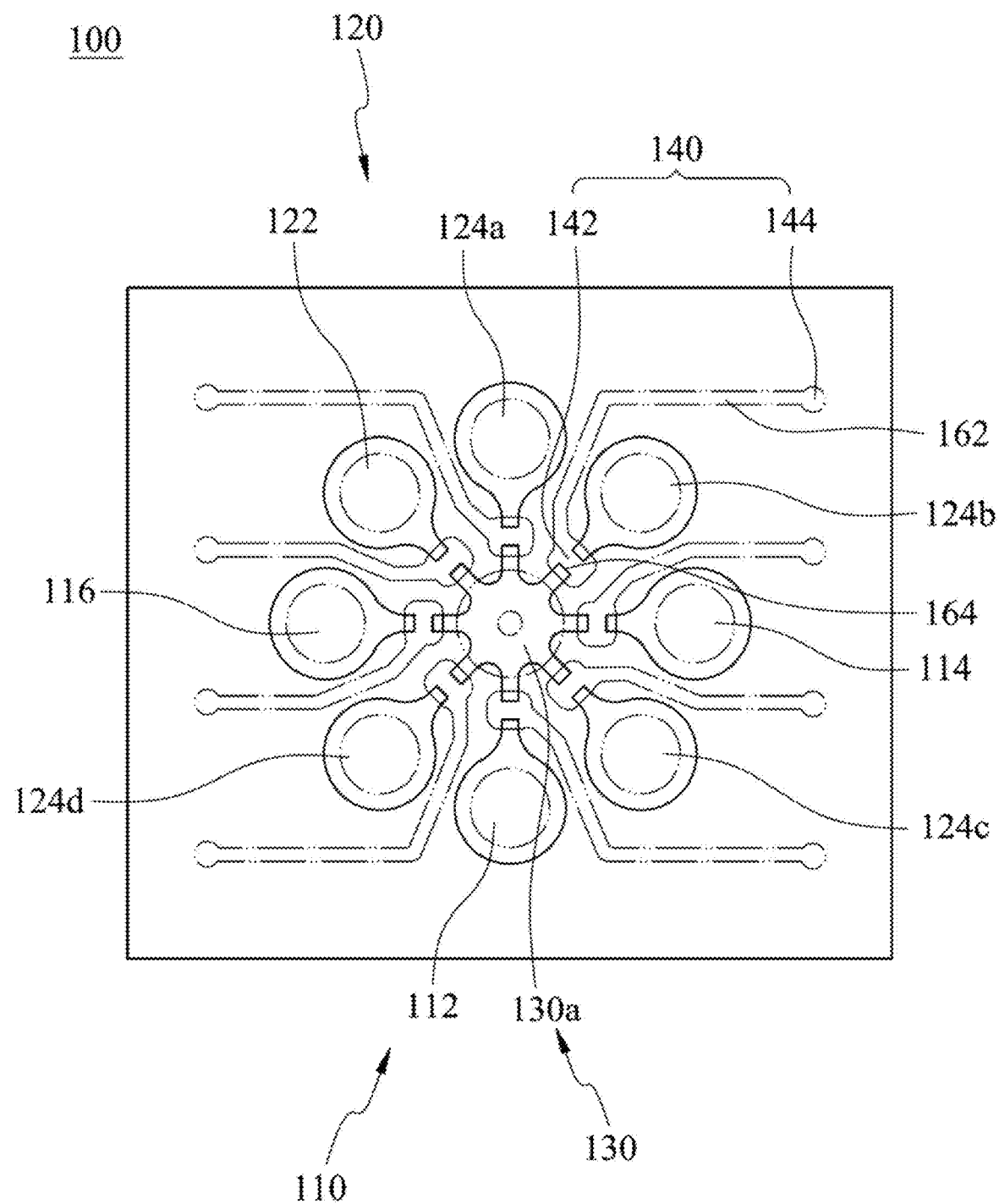
FIG. 1 is a schematic view showing a microfluidic chip according to Embodiment 1 of the present disclosure.

The present disclosure provides an automatic microfluidic system for an antibiotic susceptibility testing. Manually operated process of the conventional antibiotic susceptibility testing, such as the liquid transportation and broth dilution, can be operated automatically. Moreover, the transportation and mixing of the liquid can be performed preciously and efficiently by the integration of at least one pneumatic micro-pumping unit and pneumatic micro-valves so that the contamination can be avoided. In addition, the antibiotic susceptibility testing performed by the microfluidic system of the present disclosure can reduce the assay time and increase operation simplicity and reliability. Therefore, it is favorable for rapid screening and saving the cost of the treatment.

The microfluidic system at least includes a microfluidic chip, and the microfluidic chip can include a fluid storage unit, a reaction unit, a pneumatic micro-pumping unit and a plurality of valve units. In particular, the fluid storage unit includes a first fluid storage chamber, a second fluid storage chamber and a third fluid chamber for storing a bacterial suspension, a broth and an antibiotic solution, respectively.

The reaction unit includes a first reaction chamber and several second reaction chambers. The first reaction chamber is designed as a control group in the following antibiotic susceptibility testing, and the control group contains the broth and the bacterial suspension but does not contain the antibiotic solution. The second reaction chambers are designed as experimental groups, and each of the experimental groups can contain one antibiotic solution with a predetermined concentration or various antibiotic solutions with different concentrations. Thus, a minimum inhibitory concentration or a fractional inhibitory concentration index can be determined according to a situation in each of the second reaction chambers.

The pneumatic micro-pumping unit is adjacently disposed to the fluid storage unit and the reaction unit for repeatedly and quantitatively transporting the broth and the bacterial suspension to the first reaction chamber to form a first mixing solution and for repeatedly and quantitatively transporting the broth, the bacterial suspension and the antibiotic solution to the second reaction chambers to form at least two second mixing solutions.

The valve units include a plurality of pneumatic micro-valves and a plurality of valve control air holes. In details, the pneumatic micro-valves can be disposed between the fluid storage unit and the pneumatic micro-pumping unit, and between the pneumatic micro-pumping unit and the reaction unit. Alternatively, the pneumatic micro-valves can be disposed between pneumatic micro-pumps when the pneumatic micro-pumping unit has more than one pneumatic micro-pumps. Therefore, it minimizes sample cross-contamination during the quick liquid transportation and assist the pneumatic micro-pumping unit to transport preciously. The valve control air holes are applied for controlling the opening and closing of the pneumatic micro-valves.

It is noted that the number of the fluid storage unit, the reaction unit, the pneumatic micro-pumping unit and the valve units are designed according to the purpose of the following application. For example, the fluid storage unit can include a plurality of the third fluid storage chambers for storing more than one antibiotic solutions. However, the present disclosure is not limited thereto.

The microfluidic system of the present disclosure has been described as mentioned above. In the following, Embodiments 1 and Embodiment 2 will be further provided to illustrate the abovementioned microfluidic system, the configuration of elements and method for operating thereof in details. The performance of the microfluidic system is also disclosed in each test of the antibiotic susceptibility testing, but the present disclosure is not limited thereto.

Microfluidic System and Method for Manufacturing and Operating Thereof

Embodiment 1

In Embodiment 1, an automatic microfluidic system for an antibiotic susceptibility testing at least includes a microfluidic chip 100. Please refer to FIG. 1, which is a schematic view showing the microfluidic chip 100 according to Embodiment 1 of the present disclosure. The microfluidic chip 100 includes a fluid storage unit 110, a reaction unit 120, a pneumatic micro-pumping unit 130 and a plurality of valve units 140.

In particular, the fluid storage unit 110 includes a first fluid storage chamber 112, a second fluid storage chamber 114 and a third fluid storage chamber 116. The first fluid storage chamber 112 is designed for storing a bacterial suspension, the second fluid storage chamber 114 is designed for storing a broth, and the third fluid storage chamber 116 is designed for storing an antibiotic solution. The details of the bacterial suspension, the broth and the antibiotic solution will be illustrated as follows, and there is no further description herein.

The reaction unit 120 includes a first reaction chamber 122 and four second reaction chambers, that is, the second reaction chamber 124a, the second reaction chamber 124b, the second reaction chamber 124c and the second reaction chamber 124d. In Embodiment 1, the first reaction chamber 122 is designed as a control group in the following antibiotic susceptibility testing, which contains the broth and the bacterial suspension but does not contain the antibiotic solution. The second reaction chamber 124a, the second reaction chamber 124b, the second reaction chamber 124c and the second reaction chamber 124d are designed as experimental groups, and the experimental groups contain the antibiotic solution with different concentrations, respectively. Thus, a minimum inhibitory concentration can be determined according to a situation in each of the second reaction chambers.

The pneumatic micro-pumping unit 130 is adjacently disposed to the fluid storage unit 110 and the reaction unit 120 for repeatedly and quantitatively transporting the broth and the bacterial suspension to the first reaction chamber 122 to form a first mixing solution and for repeatedly and quantitatively transporting the broth, the bacterial suspension and the antibiotic solution to the second reaction chamber 124a, the second reaction chamber 124b, the second reaction chamber 124c and the second reaction chamber 124d to form four second mixing solutions. In particular, the pneumatic micro-pumping unit 130 includes a first pneumatic micro-pump 130a, and the fluid storage unit 110 and the reaction unit 120 are radially distributed around the first pneumatic micro-pump 130a for minimizing the dead volume and chip size of the microfluidic chip 100.

The valve units 140 includes a plurality of pneumatic micro-valves 142 and a plurality of valve control air holes 144. In details, the pneumatic micro-valves 142 are disposed between the fluid storage unit 110 and the first pneumatic micro-pump 130a. That is, the pneumatic micro-valves 142 are disposed between the first fluid storage chamber 112 and the first pneumatic micro-pump 130a, between the second fluid storage chamber 114 and the first pneumatic micro-pump 130a, and between the third fluid storage chamber 116 and the first pneumatic micro-pump 130a. Moreover, the pneumatic micro-valves 142 are also disposed between the first pneumatic micro-pump 130a and the reaction unit 120. That is, the pneumatic micro-valves 142 are also disposed between the first pneumatic micro-pump 130a and the first reaction chamber 122 and between the first pneumatic micro-pump 130a and each of the second reaction chamber 124a, the second reaction chamber 124b, the second reaction chamber 124c and the second reaction chamber 124d. Therefore, it minimizes sample cross-contamination during the quick liquid transportation and assist the pneumatic micro-pumping unit 130 to transport preciously. The valve control air holes 144 are applied for controlling the opening and closing of the pneumatic micro-valves 142. In Embodiment 1, the pneumatic micro-valves 142 are normally-closed micro-valves.

Figure 2:
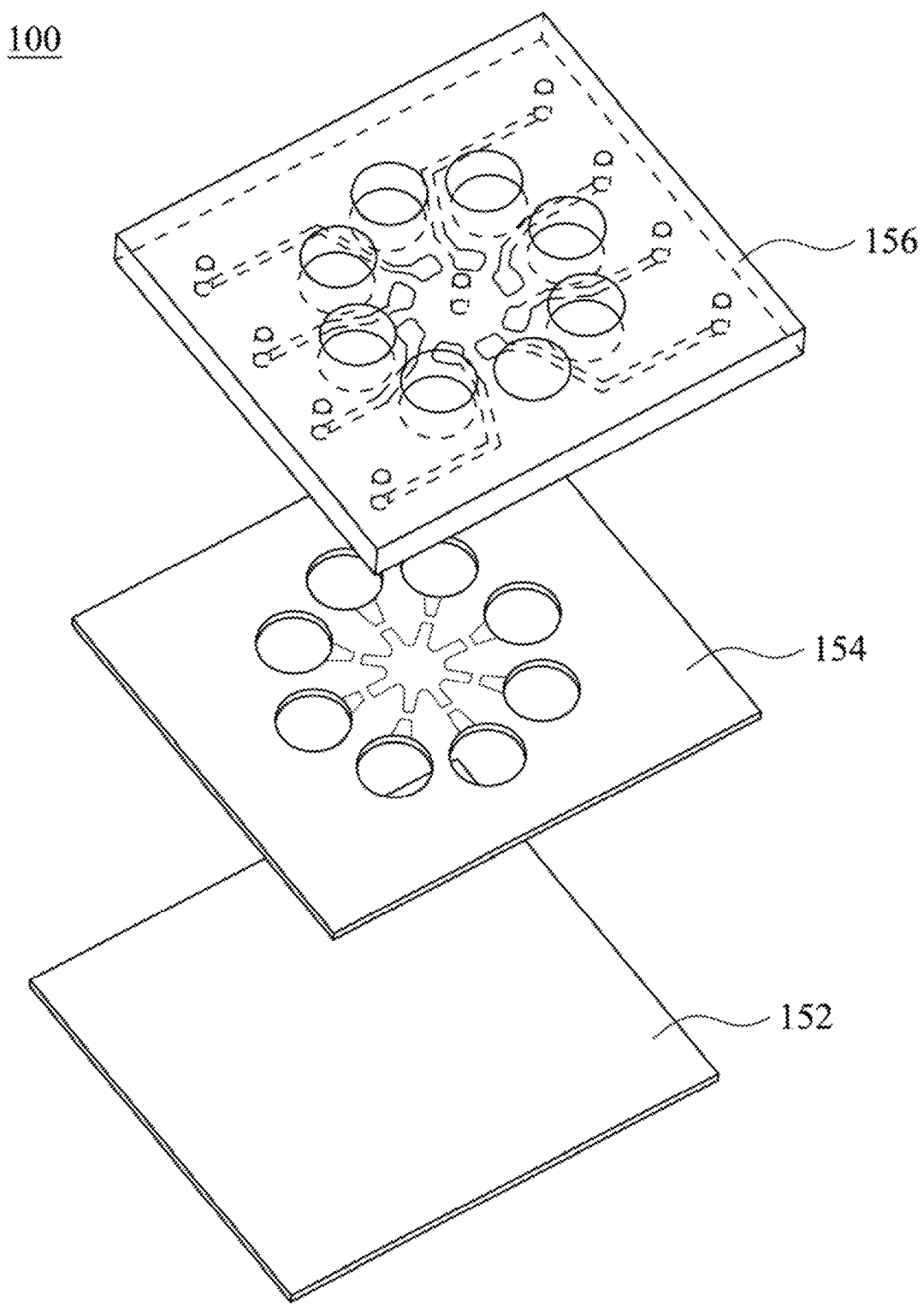
FIG. 2 is an exploded view of the microfluidic chip of FIG. 1.
Figure 4:
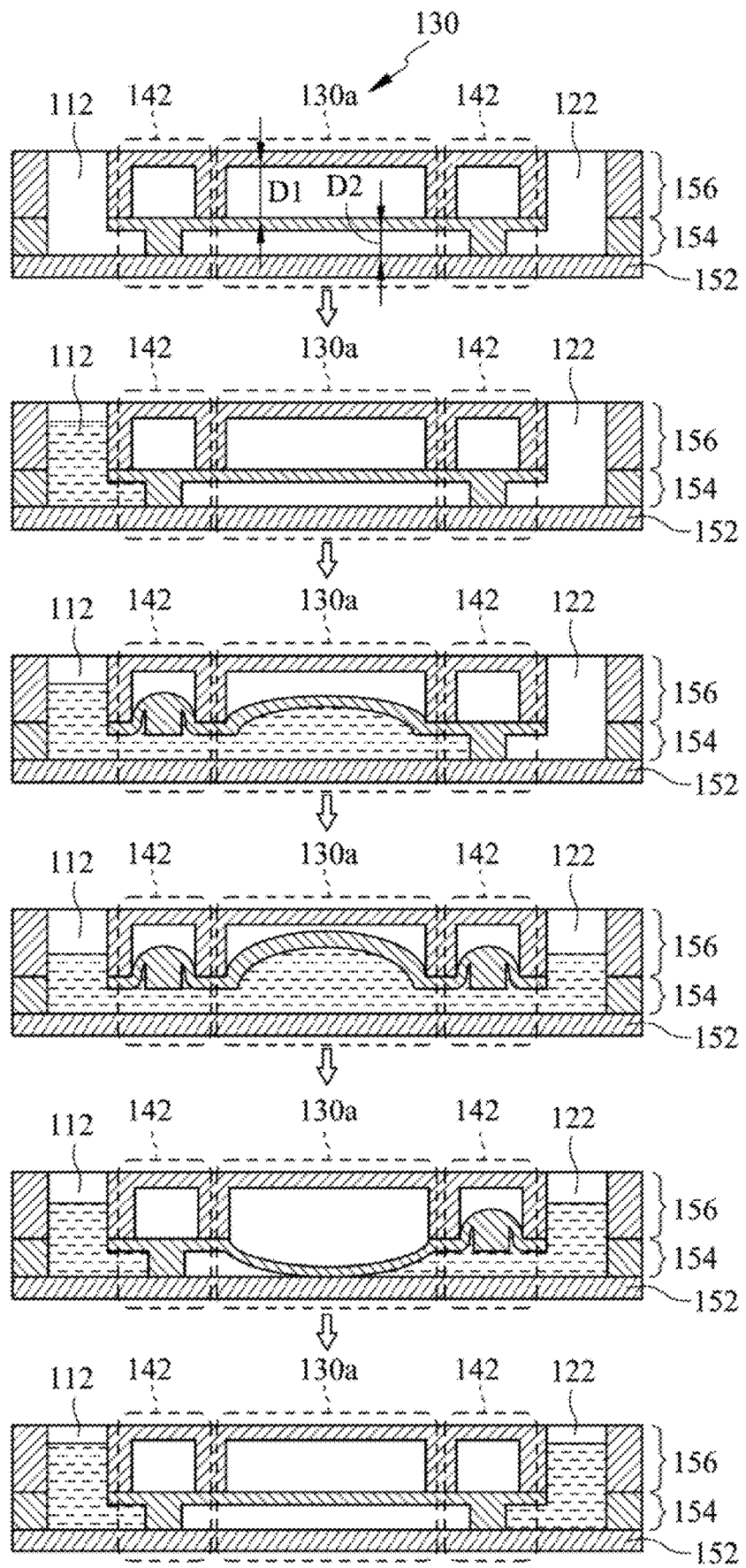
FIG. 4 is a schematic side view of fluid flow in the microfluidic chip of FIG. 1.

Please refer to FIG. 2 in conjunction with FIG. 4. FIG. 2 is an exploded view of the microfluidic chip 100 of FIG. 1, and FIG. 4 is a schematic side view of fluid flow in the microfluidic chip 100 of FIG. 1. As shown in FIG. 2, the microfluidic chip 100 is composed of a substrate 152, a first flexible material layer 154 and a second flexible material layer 156 from bottom to top. Moreover, the substrate 152, the first flexible material layer 154 and the second flexible material layer 156 are configured to define an air channel layer and a liquid channel layer. The air channel layer is a cavity between the first flexible material layer 154 and the second flexible material layer 156 for transporting air, and the liquid channel layer is a cavity between the substrate 152 and the first flexible material layer 154 for transporting liquid. More particularly, the air channel layer includes a plurality of air channels 162, and the liquid channel layer includes a plurality of liquid channels 164. As shown in FIG. 4, the air channel layer and the liquid channel layer are further configured to define the pneumatic micro-pumping unit 130 and the pneumatic micro-valves 142.

The substrate 152 is made of glass, and the first flexible material layer 154 and the second flexible material layer 156 are both made of poly(dimethylsiloxane) (PDMS). Therefore, the microfluidic chip has advantages, such as low cost, simplified manufacturing process, disposable and mass-producible. In Embodiment 1, a thickness of the substrate 152 of the microfluidic chip 100 is 0.7 mm, and thicknesses of the first flexible material layer 154 and the second flexible material layer 156 are 0.3 mm and 10 mm, respectively. Moreover, a thickness D1 of the air channel layer is 0.2 mm, and a thickness D2 of the liquid channel layer is 0.2 mm. However, the present disclosure is not limited thereto.

Figure 3:
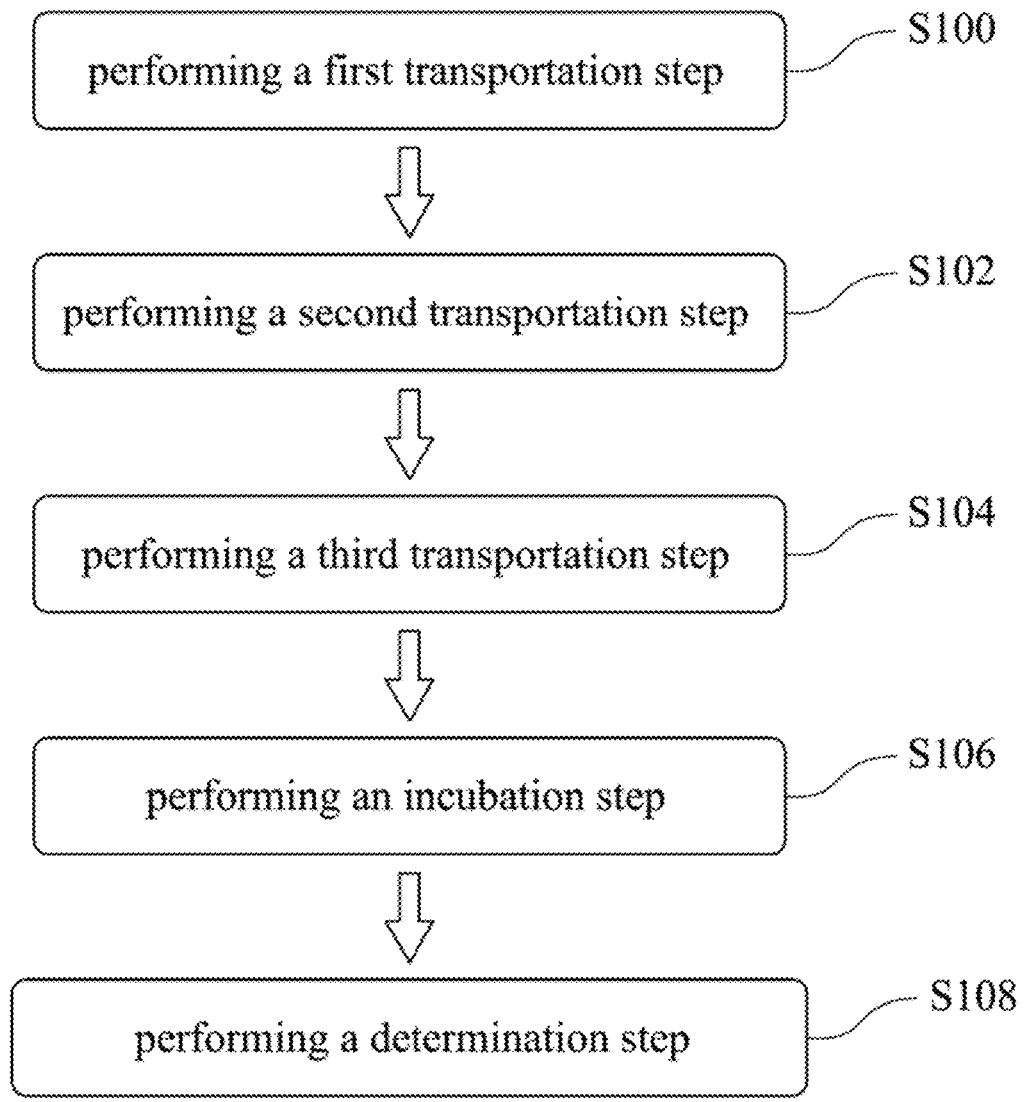
FIG. 3 is a flow chart showing a method for operating the microfluidic chip of FIG. 1.

FIG. 3 is a flow chart showing a method for operating the microfluidic chip 100 of FIG. 1 and then referred in conjunction with FIG. 4. The method includes Step S100, Step S102, Step S104, Step S106 and Step S108.

In the antibiotic susceptibility testing, reagents to be tested (the bacterial suspension, the broth and the antibiotic solution with a specific concentration) are loaded to the first fluid storage chamber 112, the second fluid storage chamber 114 and the third fluid storage chamber 116, separately.

Step S100 is a first transportation step. In Step S100, the first pneumatic micro-pump 130a of the pneumatic micro-pumping unit 130 repeatedly and quantitatively transports the bacterial suspension from the first fluid storage chamber 112 to the first reaction chamber and each of the second reaction chamber 124a, the second reaction chamber 124b, the second reaction chamber 124c and the second reaction chamber 124d. FIG. 4 shows a fluid flow from the first fluid storage chamber 112 to the first reaction chamber 122. It is noted that a fluid flow from the first fluid storage chamber 112 to each of the second reaction chamber 124a, the second reaction chamber 124b, the second reaction chamber 124c and the second reaction chamber 124d and a fluid flow from the second fluid storage chamber 114 or the third fluid storage chamber 116 to each of the second reaction chamber 124a, the second reaction chamber 124b, the second reaction chamber 124c and the second reaction chamber 124d are similar. In details, after the bacterial suspension is loaded in the first fluid storage chamber 112, air is supplied by one of the valve control air holes 144 close to the first fluid storage chamber 112. Then, the pneumatic micro-valves 142 and the membrane of the first pneumatic micro-pump 130a are elevated by a suction force (that is, a negative gauge pressure) caused by vacuum so that the bacterial suspension in the first fluid storage chamber 112 flows into the first pneumatic micro-pump 130a via the fluid channel 164. Next, air is supplied by one of the valve control air holes 144 close to the first reaction chamber 122 of the reaction unit 120, and another one of the pneumatic micro-valves 142 is elevated so that the bacterial suspension in the first pneumatic micro-pump 130a flows into the first reaction chamber 122 via the fluid channel 164. Finally, compressed air (that is, a positive gauge pressure) is supplied to the first pneumatic micro-pump 130a to push all the bacterial suspension into the first reaction chamber 122. Similarly, the bacterial suspension can be transported from the first fluid storage chamber 112 to each of the second reaction chamber 124a, the second reaction chamber 124b, the second reaction chamber 124c and the second reaction chamber 124d by the abovementioned method. After Step S100, a cleaning step (not shown in the figure) can be performed for transporting the broth to the first pneumatic micro-pump 130a to clean the first pneumatic micro-pump 130a. A waste liquid recycling step (not shown in the figure) can be further performed for recycling the broth to the first fluid storage chamber 112. Therefore, the first fluid storage chamber 112 can be fully utilized when it is empty and an additional waste tank is omitted.

In addition, the liquid, which is transported from the fluid storage unit 110 to the reaction unit 120 by the microfluidic chip 100, is a fixed volume during each transportation. That is, by means of the configuration, such as the pneumatic micro-pumping unit 130 and the pneumatic micro-valve 142, and the cooperation between the positive gauge pressure and the negative gauge pressure, the microfluidic chip 100 can transport the fixed volume of the liquid from the fluid storage unit to the reaction unit without the sample cross-contamination every time. In particular, each of the first reaction chamber 122, the second reaction chamber 124a, the second reaction chamber 124b, the second reaction chamber 124c and the second reaction chamber 124d can obtain 4.2 μL of the fluid after each transportation when an applied gauge pressure of the suction force is 60 kPa and an applied gauge pressure of the push force is 35 kPa. Thus, Step S100 can be repeated for five times if each of the first reaction chamber 122, the second reaction chamber 124a, the second reaction chamber 124b, the second reaction chamber 124c and the second reaction chamber 124d wants to obtain 21 μL of the bacterial suspension.

Step S102 is a second transportation step. In Step S102, the first pneumatic micro-pump 130a transports the broth to the first reaction chamber 122 and each of the second reaction chamber 124a, the second reaction chamber 124b, the second reaction chamber 124c and the second reaction chamber 124d. In details, a volume of the broth in the first reaction chamber 122 is a1, a volume of the broth in the second reaction chamber 124a is a2, a volume of the broth in the second reaction chamber 124b is a3, a volume of the broth in the second reaction chamber 124c is a4, and a volume of the broth in the second reaction chamber 124d is a5. That is, the broth is added to the first reaction chamber 122 and each of the second reaction chamber 124a, the second reaction chamber 124b, the second reaction chamber 124c and the second reaction chamber 124d, respectively, by a first ratio of a1 to a2 to a3 to a4 to a5. It is noted the volume of the bacterial suspension in each of the first reaction chamber 122, the second reaction chamber 124a, the second reaction chamber 124b, the second reaction chamber 124c and the second reaction chamber 124d are the same. Moreover, the transportation and the mixing of the bacterial suspension and the broth are performed at the same time. As mentioned above, the liquid, which is transported from the fluid storage unit 110 to the reaction unit 120 by the microfluidic chip 100, is the fixed volume during each transportation. Therefore, the first ratio of a1 to a2 to a3 to a4 to a5 can be adjusted by a frequency of transporting the broth to the first reaction chamber 122 and each of the second reaction chamber 124a, the second reaction chamber 124b, the second reaction chamber 124c and the second reaction chamber 124d.

Step S104 is a third transportation step. In Step S104, the antibiotic solution with a suitable initial concentration is transported from the third fluid storage chamber 116 to at least one of the second reaction chamber 124a, the second reaction chamber 124b, the second reaction chamber 124c and the second reaction chamber 124d by the first pneumatic micro-pump 130a. In details, a volume of the antibiotic solution in the first reaction chamber 122 is b1, a volume of the antibiotic solution in the second reaction chamber 124a is b2, a volume of the antibiotic solution in the second reaction chamber 124b is b3, a volume of the antibiotic solution in the second reaction chamber 124c is b4, and a volume of the antibiotic solution in the second reaction chamber 124d is b5. That is, the antibiotic solution is added to each of the first reaction chamber 122, the second reaction chamber 124a, the second reaction chamber 124b, the second reaction chamber 124c and the second reaction chamber 124d, respectively, by a second ratio of b1 to b2 to b3 to b4 to b5. Moreover, the transportation and the mixing of the antibiotic solution and the abovementioned mixing solution are performed at the same time.

In addition, the first ratio and the second ratio satisfy the following condition: (a1+b1)=(a2+b2)=(a3+b3)=(a4+b4)=(a5+b5). For example, when the broth is added to each of the first reaction chamber 122, the second reaction chamber 124a, the second reaction chamber 124b, the second reaction chamber 124c and the second reaction chamber 124d in Step S102 by the first ratio of 5 to 4 to 3 to 2 to 1, the antibiotic solution added will be added to each of the first reaction chamber 122, the second reaction chamber 124a, the second reaction chamber 124b, the second reaction chamber 124c and the second reaction chamber 124d in Step S104 by the second ratio of 0 to 1 to 2 to 3 to 4.

Accordingly, a solution in the first reaction chamber 122 does not contain the antibiotic solution, that is, the first mixing solution. In the meanwhile, solutions in the second reaction chamber 124a, the second reaction chamber 124b, the second reaction chamber 124c and the second reaction chamber 124d are the second mixing solutions. Similarly, the second ratio of b1 to b2 to b3 to b4 to b5 can be adjusted by a frequency of transporting the antibiotic solution to the first reaction chamber 122 and each of the second reaction chamber 124a, the second reaction chamber 124b, the second reaction chamber 124c and the second reaction chamber 124d. Thus, a concentration of the antibiotic solution in each of the second mixing solutions is adjusted by a frequency of transporting the antibiotic solution and the broth.

Step S106 is an incubation step. In Step S106, the first mixing solution and each of the second mixing solutions are allowed to stand for an incubation time. In particular, a temperature of the microfluidic chip 100 can be controlled in a predetermined range in Step S106. That is, the microfluidic system can further include a temperature control apparatus (not shown in the figure) for controlling the temperature of the microfluidic chip 100. Preferably, the temperature control apparatus is a thermos plate disposed under the microfluidic chip 100. Alternatively, the temperature control apparatus is an incubator for containing the microfluidic chip 100.

Finally, Step S108 is a determination step. In Step S108, a minimum inhibitory concentration of the abovementioned antibiotic solution for bacteria to be tested can be determined.

In particular, Step S108 can be performed by detecting an absorbance detection method or a fluorescent performance of live bacteria. For example, the microfluidic system of the present disclosure can further include an absorbance detection device (not shown in the figure) for detecting an optical density of the first mixing solution and an optical density of each of the second mixing solutions, after the incubation time.

Alternatively, Step S108 can further include the following steps (not shown in the figure). First, a dye is added into the first mixing solution and each of the second mixing solutions. A fluorescence detection step is then performed for determining a minimum concentration without live bacteria of the second mixing solutions.

Alternatively, the broth can include a pH indicator. It is noted that the pH-dependent colorimetric broth will be transformed into an acidic pH due to bacterial growth. Preferably, a pH range for color change of the pH indicator is ranged from pH 6.0 to pH 8.0. Thus, Step S108 can be applied for determining a minimum concentration without color change of the second mixing solutions. Therefore, a colorimetric means of determining the minimum inhibitory concentration by eye is feasible on-chip, as a media color change is indicative of bacterial growth. Such simplified operations can replace the conventional method, such as the fluorescent staining and an additional microscopy, so as to lead to a reduction in human error.

The method for operating the microfluidic system of the present disclosure is described as above and achieved via a proportional dilution mode according to the CLSI guidelines. However, the microfluidic system of the present disclosure also can be operated with a serial dilution mode for demand.

Figure 5A:
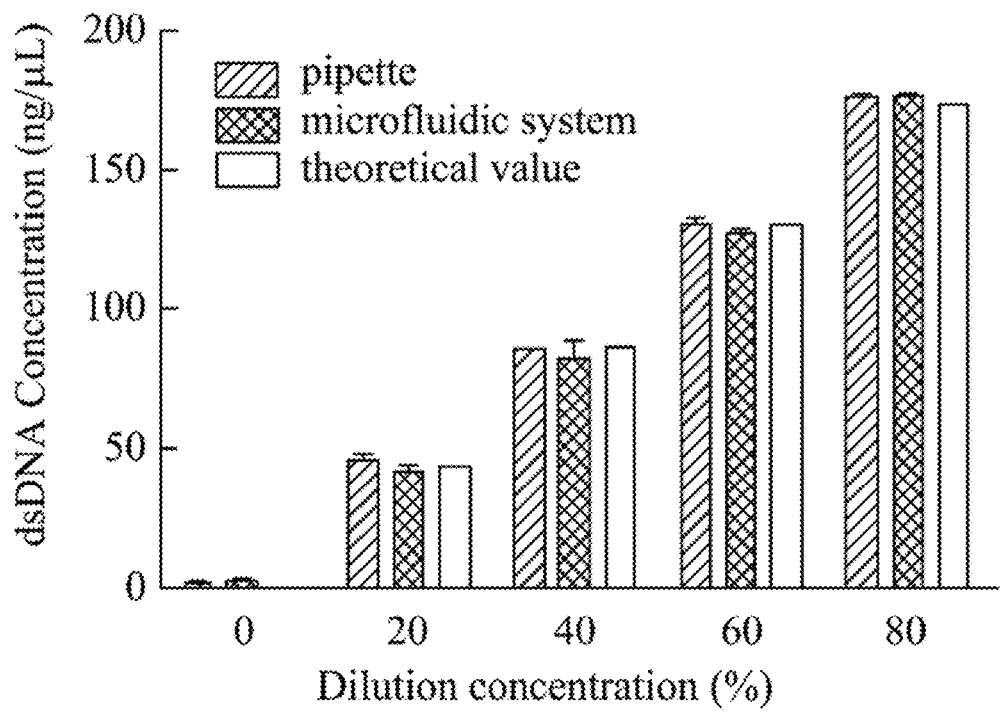
FIG. 5A is a quantitative performance of the microfluidic chip of FIG. 1 in comparison to a pipette and a theoretical value by diluting double-stranded DNA (hereafter referred as dsDNA) with a proportional dilution mode.
Figure 5B:
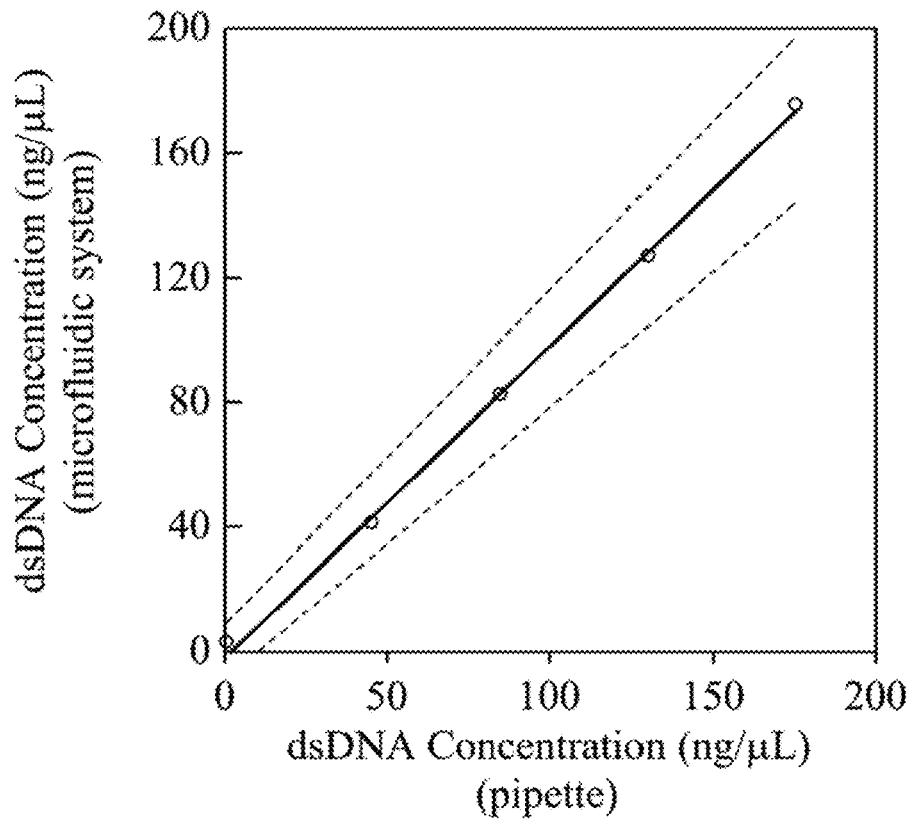
FIG. 5B is a comparison result between the microfluidic chip of FIG. 1 and the pipette by processing FIG. 5A via a passing-bablok regression analysis.
Figure 5C:
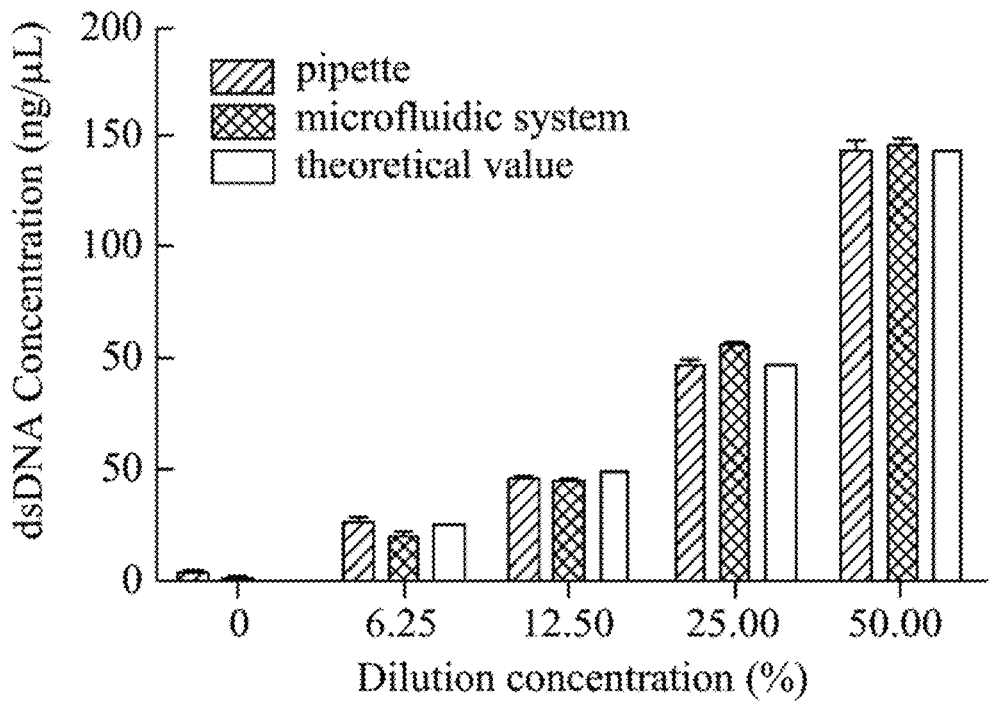
FIG. 5C is a quantitative performance of the microfluidic chip of FIG. 1 in comparison to a pipette and a theoretical value by diluting the dsDNA with a two-fold serial dilution mode.
Figure 5D:
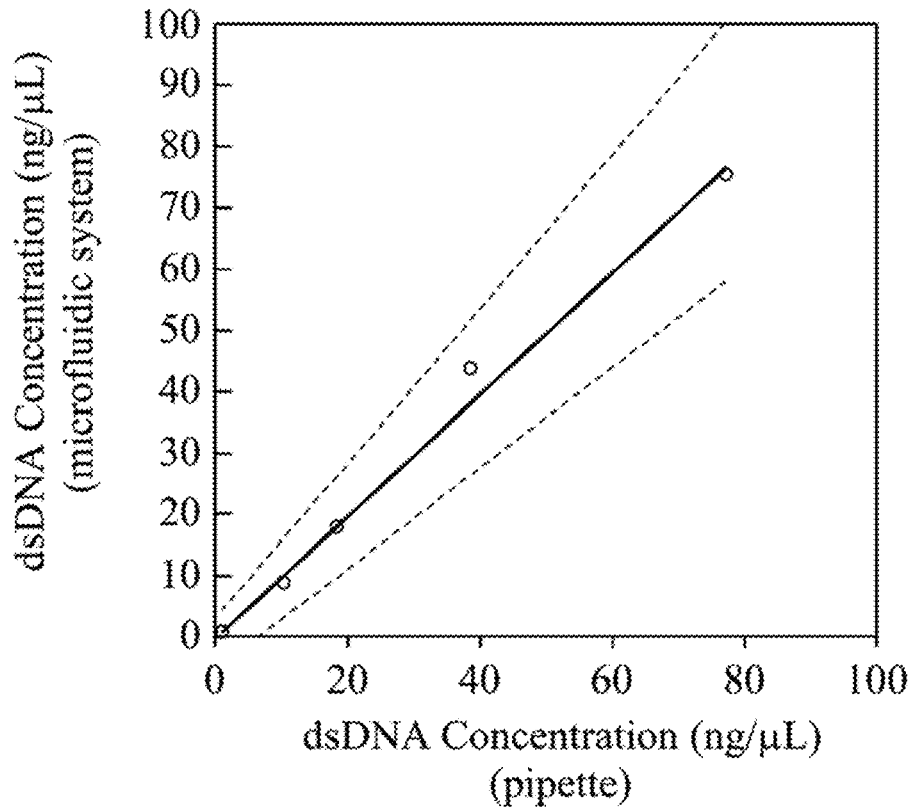
FIG. 5D is a comparison result between the microfluidic chip of FIG. 1 and the pipette by processing FIG. 5C via the passing-bablok regression analysis.

Please refer to FIG. 5A-5D. FIG. 5A and FIG. 5C are quantitative performances of the microfluidic chip of FIG. 1 in comparison to a pipette and a theoretical value by diluting dsDNA (n=5) with a proportional dilution mode and a two-fold serial dilution mode, respectively. FIG. 5B and FIG. 5D are comparison results between the microfluidic chip of FIG. 1 and the pipette by processing FIG. 5A and FIG. 5C, separately, via a passing-bablok regression analysis.

In details, the present disclosure uses the dsDNA as a reagent to be diluted. Because a linear proportional relationship is existed between concentrations of the dsDNA and optical densities thereof in a specific concentration range, the concentration of the dsDNA can be obtained from the optical density by a spectrophotometer. Then, the dsDNA can be used as a reference solution and diluted automatically by the microfluidic system. In the meanwhile, a large system, such as the pipette, is applied as a verification for performing a manual dilution process.

In FIG. 5A and FIG. 5C, the dilution performances both show excellent agreement among the microfluidic system, the pipette and the theoretical value for the dilution of the dsDNA in both proportional dilution mode and serial dilution mode. In FIG. 5B and FIG. 5D, the comparison results both fall within a 95% confidence interval (CI). That is, the concentrations of the dsDNA diluted by the microfluidic device are consistent with those obtained by the manual pipette. Thus, the abovementioned data give evidence of the performance of the microfluidic system of the present disclosure, and the microfluidic system can replace the manual system to perform a quantitative testing preciously and automatically. Furthermore, the two dilution modes can be used optionally so as to avoid the human error and increase the flexibility and steerability of the microfluidic system.

Embodiment 2

In Embodiment 2, another automatic microfluidic system for antibiotic susceptibility testing at least includes a microfluidic chip 100'. Please refer to FIG. 6, which is a schematic view showing the microfluidic chip 100' according to Embodiment 2 of the present disclosure. The configuration of the microfluidic chip 100' is similar to the microfluidic chip 100 of Embodiment 1. That is, the microfluidic chip 100' includes a fluid storage unit 110', a reaction unit 120', a pneumatic micro-pumping unit 130' and a plurality of valve units 140'. In Embodiment 2, quantities of elements, such as first fluid storage chambers, a second fluid storage chambers and third fluid storage chambers of the fluid storage unit 110' and pneumatic micro-pumps of the pneumatic micro-pumping unit 130', and the configuration between the elements are different from Embodiment 1.

In particular, the fluid storage unit 110' includes a first fluid storage chamber 112', a second fluid storage chamber 114' and two third fluid storage chamber 116a', 116b'. The first fluid storage chamber 112' is designed for storing a bacterial suspension, the second fluid storage chamber 114' is designed for storing a broth, the third fluid storage chamber 116a' is designed for storing one antibiotic solution, and the third fluid storage chamber 116b' is designed for storing the other antibiotic solution. The details of the bacterial suspension, the broth and the two antibiotic solutions will be illustrated as follows, and there is no further description herein.

The reaction unit 120' includes a first reaction chamber 122' and eleven second reaction chambers 124a', 124b', 124c', 124d', 124e', 124f', 124g', 124h', 124i', 124j' and 124k'. In Embodiment 2, the first reaction chamber 122' is also designed as a control group in the following antibiotic susceptibility testing, which contains the broth and the bacterial suspension but does not contain the antibiotic solution. The second reaction chambers 124a', 124b', 124c', 124d', 124e', 124f', 124g', 124h', 124i', 124j' and 124k' are designed as experimental groups, and the experimental groups contain the two antibiotic solutions with different concentrations, respectively. Thus, a quantitative estimate of the activities of the two antibiotic solutions in combination against antibiotics-resistant bacteria can be determined according to a situation in each of the second reaction chambers.

The pneumatic micro-pumping unit 130' includes two first pneumatic micro-pumps 130a' and two second pneumatic micro-pumps 130b' communicated with each other. In particular, one of the two first pneumatic micro-pumps 130a' is connected to the first fluid storage chamber 112', the first reaction chamber 122' and the second reaction chambers 124a', 124b', 124c', 124d' and 124e'. The other of the two first pneumatic micro-pumps 130a' is connected to the second reaction chambers 124f', 124g', 124h', 124i', 124j' and 124k'. Moreover, the second pneumatic micro-pumps 130b' are connected to the second fluid storage chamber 114', the third fluid storage chamber 116a' and the third fluid storage chamber 116b', respectively. In Embodiment 2, the fluid storage unit 110' and the reaction unit 120' of the microfluidic chip 100' are radially distributed around the first pneumatic micro-pumps 130a' and the second pneumatic micro-pumps 130b' for minimizing the dead volume and chip size of the microfluidic chip 100'.

The valve units 140' includes a plurality of pneumatic micro-valves 142' and a plurality of valve control air holes 144'. In Embodiment 2, the valve units 140' can be further disposed between the first pneumatic micro-pumps 130a' and the second pneumatic micro-pumps 130b'. In particular, the pneumatic micro-valves 142' of Embodiment 2 are normally-dosed micro-valves.

A method for operating the microfluidic chip 100' of Embodiment 2 is approximately the same as Embodiment 1. Thus, the abovementioned method can be described referring to FIG. 3.

In Step S100 (that is, the first transportation step), the first pneumatic micro-pumps 130a' of the pneumatic micro-pumping unit 130' repeatedly and quantitatively transport the bacterial suspension from the first fluid storage chamber 112' to each of the first reaction chamber 122' and the second reaction chambers 124a', 124b', 124c', 124d', 124e', 124f', 124g', 124h', 124i', 124j' and 124k'.

In Step S102 (that is, the second transportation step), the broth is transported to the first reaction chamber 122' and each of the second reaction chambers 124a', 124b', 124c', 124d', 124e', 124f', 124g', 124h', 124i', 124j' and 124k' and mixed with the bacterial suspension therein by the second pneumatic micro-pumps 130b' and the first pneumatic micro-pumps 130a' of the pneumatic micro-pumping 130' in turn. At that time, a solution in the first reaction chamber 122' is a first mixing solution.

In Step S104 (that is, the third transportation step), the two antibiotic solutions are transported to at least one of the second reaction chambers 124a', 124b', 124c', 124d', 124e', 124f', 124g', 124h', 124i', 124j' and 124k' and mixed by the second pneumatic micro-pumps 130b' and the first pneumatic micro-pumps 130a' of the pneumatic micro-pumping 130', respectively. Therefore, a plurality of second mixing solutions are obtained. Concentrations of the antibiotic solution and the other antibiotic solution in each of the second mixing solutions is adjusted by a frequency of transporting the antibiotic solution, the other antibiotic solution and the broth to each of the second reaction chambers 124a', 124b', 124c', 124d', 124e', 124f', 124g', 124h', 124i', 124j' and 124k'. The details are described in Embodiment 1, and there is no further description herein.

In Step S106, that is, the incubation step, the first mixing solution and each of the second mixing solutions are allowed to stand for an incubation time. In particular, a temperature of the microfluidic chip 100' can be controlled in a predetermined range in Step S106. The details has been described as above and there is no further description herein.

Finally, Step S108 is the determination step for determining a combined inhibitory concentration of the two antibiotic solutions for the bacteria to be tested. Then, a fractional inhibitory concentration of the two antibiotic solutions can be obtained.

Furthermore, the broth can include a pH indicator. It is noted that the pH-dependent colorimetric broth will be transformed into an acidic pH due to bacterial growth. Preferably, a pH range for color change of the pH indicator is ranged from pH 6.0 to pH 8.0. Thus, Step S108 can be applied for determining a minimum concentration without color change of the second mixing solutions. Therefore, a colorimetric means of determining the minimum inhibitory concentration by eye is feasible on-chip, as a media color change is indicative of bacterial growth. Such simplified operations can replace the conventional method, such as the fluorescent staining and an additional microscopy, so as to lead to a reduction in human error.

Figure 6:
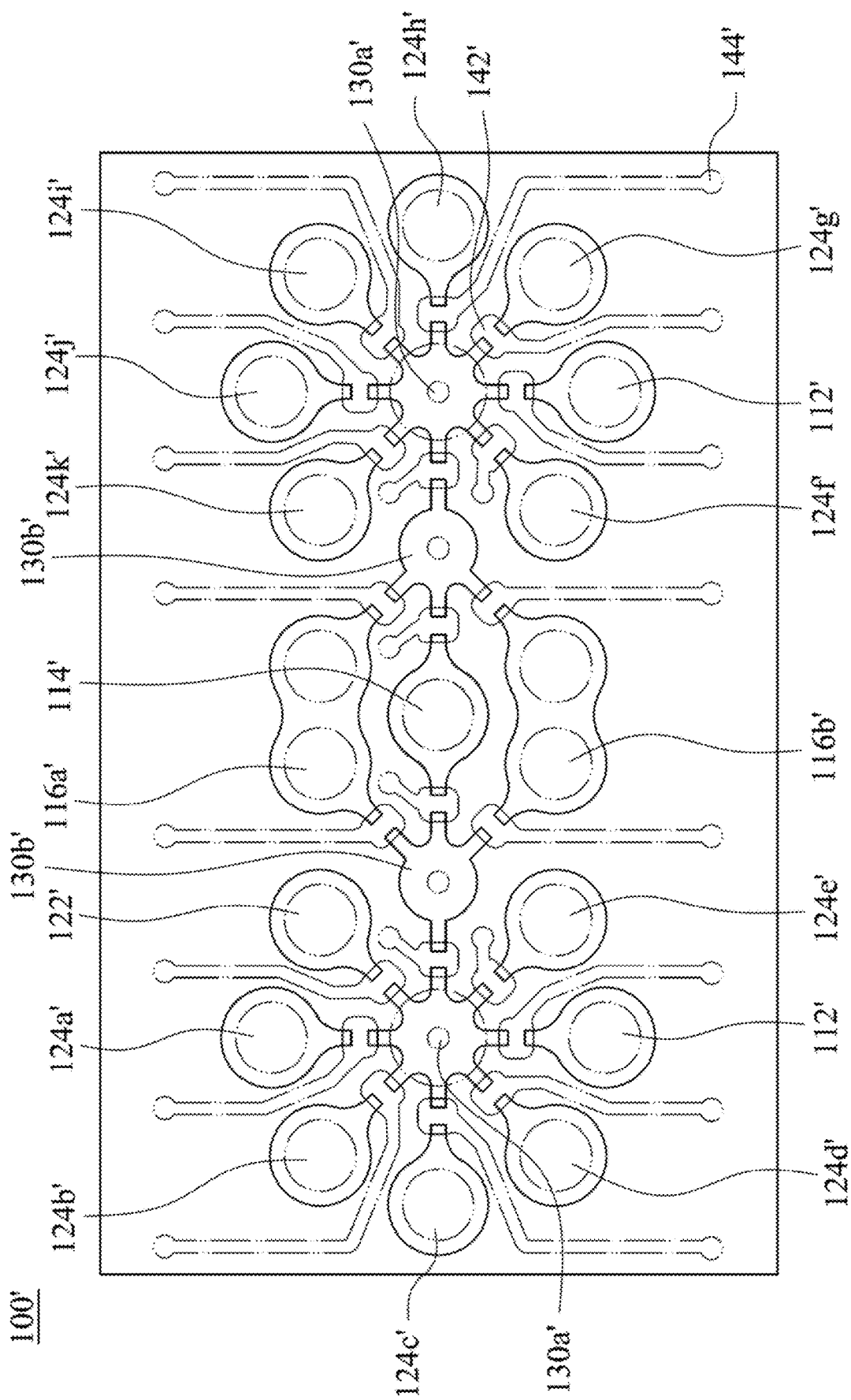
FIG. 6 is a schematic view showing a microfluidic chip according to Embodiment 2 of the present disclosure.
Figure 7A:
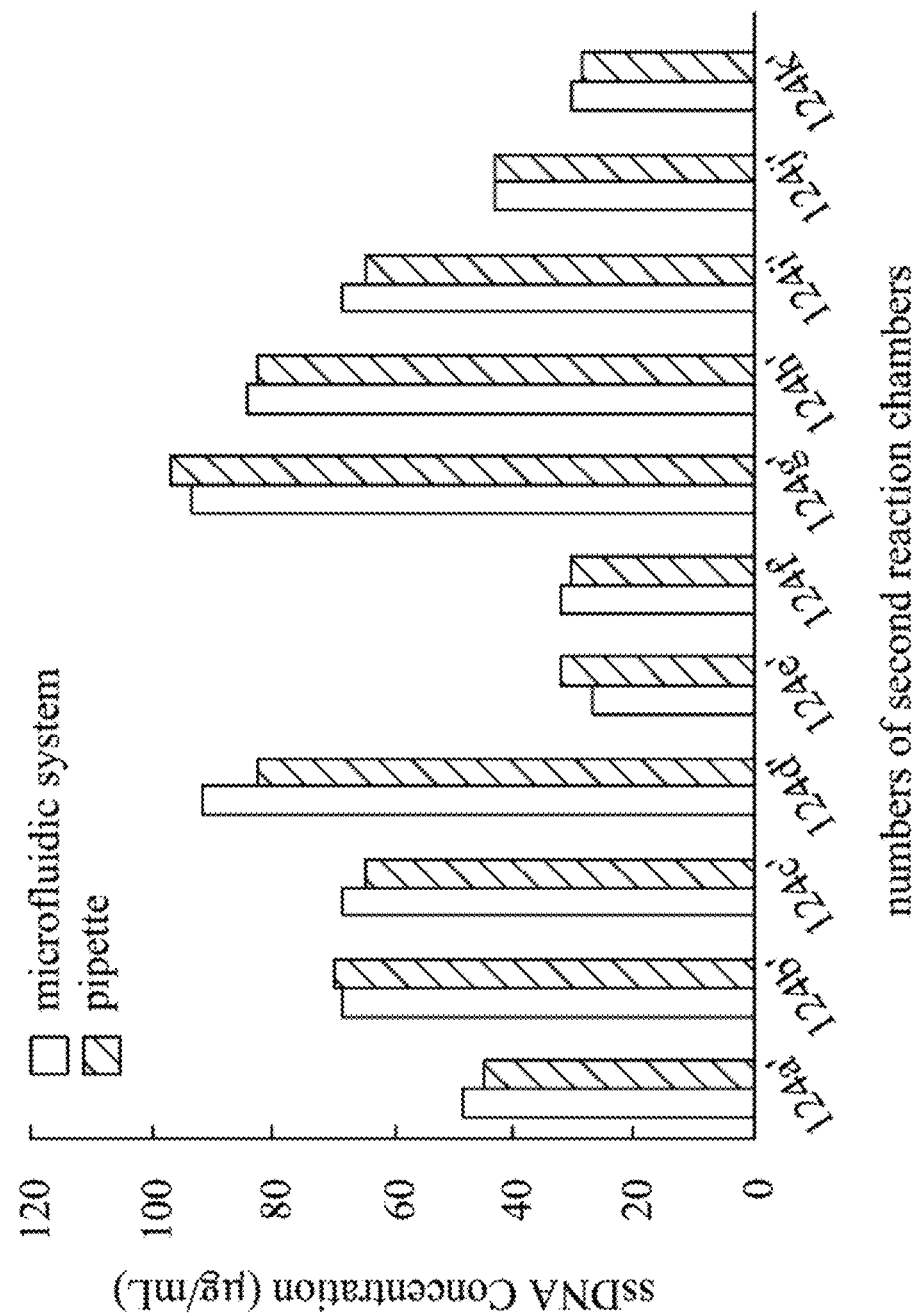
FIG. 7A is a quantitative performance of the microfluidic chip of FIG. 6 in comparison to a pipette by diluting single-stranded DNA (hereafter referred as ssDNA) with a proportional dilution mode.
Figure 7B:
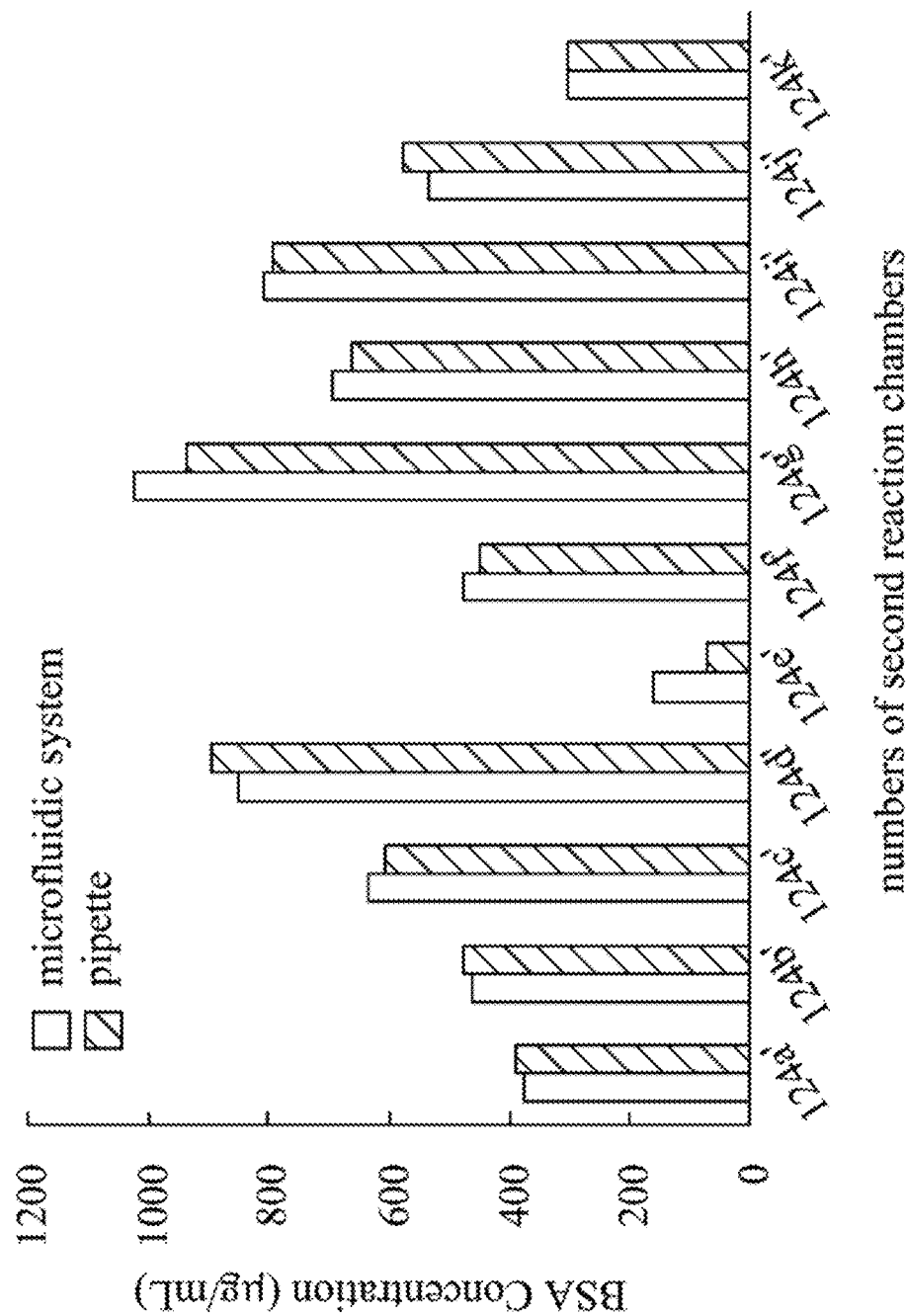
FIG. 7B is a quantitative performance of the microfluidic chip of FIG. 6 in comparison to a pipette by diluting bovine serum albumin (hereafter referred as BSA) with a proportional dilution mode.

Please refer to FIG. 7A and FIG. 7B. FIG. 7A is a quantitative performance of the microfluidic chip of FIG. 6 in comparison to a pipette by diluting ssDNA with a proportional dilution mode, and FIG. 7B is a quantitative performance of the microfluidic chip of FIG. 6 in comparison to a pipette by BSA with a proportional dilution mode. In Embodiment 2, the ssDNA and BSA are designed as a reagent to be diluted. Because a linear proportional relationship is existed between concentrations of the ssDNA and optical densities thereof in a specific concentration range, the concentration of the ssDNA can be obtained from the optical density by the spectrophotometer. Then, the ssDNA can be used as a reference solution and diluted automatically by the microfluidic system. Similarly, a linear proportional relationship is also existed between concentrations of the BSA and optical densities thereof in a specific concentration range, the concentration of the BSA can be obtained from the optical density by the spectrophotometer. Then, the BSA can be used as a reference solution and diluted automatically by the microfluidic system. In the meanwhile, a large system, such as the pipette, is applied as a verification for performing a manual dilution process of the ssDNA or the BSA.

As shown in FIG. 7A and FIG. 7B, the dilution performances both show excellent agreement between the microfluidic system and the pipette for the dilution of the ssDNA and the BSA in proportional dilution mode. Thus, the abovementioned data give evidence of the performance of the microfluidic system of Embodiment 2 in the present disclosure, and such the microfluidic system also can replace the manual system to perform a quantitative testing preciously and automatically for avoiding the human error.

In the following, Tests 1 through 6 are provided to present the performance of the abovementioned microfluidic system for the antibiotic susceptibility testing in details.

Antibiotic Susceptibility Testing

Test 1

*Enterococcus* includes 18 species. Two species of *Enterococcus* are common: *E. faecalis* (85%~90%) and *E. faecium* (10%~15%), and other rare species can be *E. gallinarum* and *E. casseliflavus*.

In Test 1, a standard strain *Enterococcus* 29212, which includes *E. faecalis* and is purchased from American type culture collection (ATCC), is designed as a bacterial suspension to be tested. The standard strain *Enterococcus* 29212 is susceptible *Enterococcus*, and a minimum inhibitory concentration of the standard strain *Enterococcus* 29212 detected by a clinical standard (i.e., E-Test®) is 4 µg/mL. In particular, the antibiotic solution of Test 1 is a vancomycin-containing solution.

Briefly, five different concentrations of antibiotic solutions (0 µg/mL, 2 µg/mL, 4 µg/mL, 6 µg/mL, and 8 µg/mL) are prepared, separately, by the microfluidic system of Embodiment 1 of the present disclosure with the proportional dilution mode. Then, the antibiotic solutions are mixed with the bacteria suspensions at a final concentration of $5 \times 10^5$ CFU/mL. The determination of the minimum inhibitory concentration is read after incubation at 37° C. for 24 hours.

Figure 8:
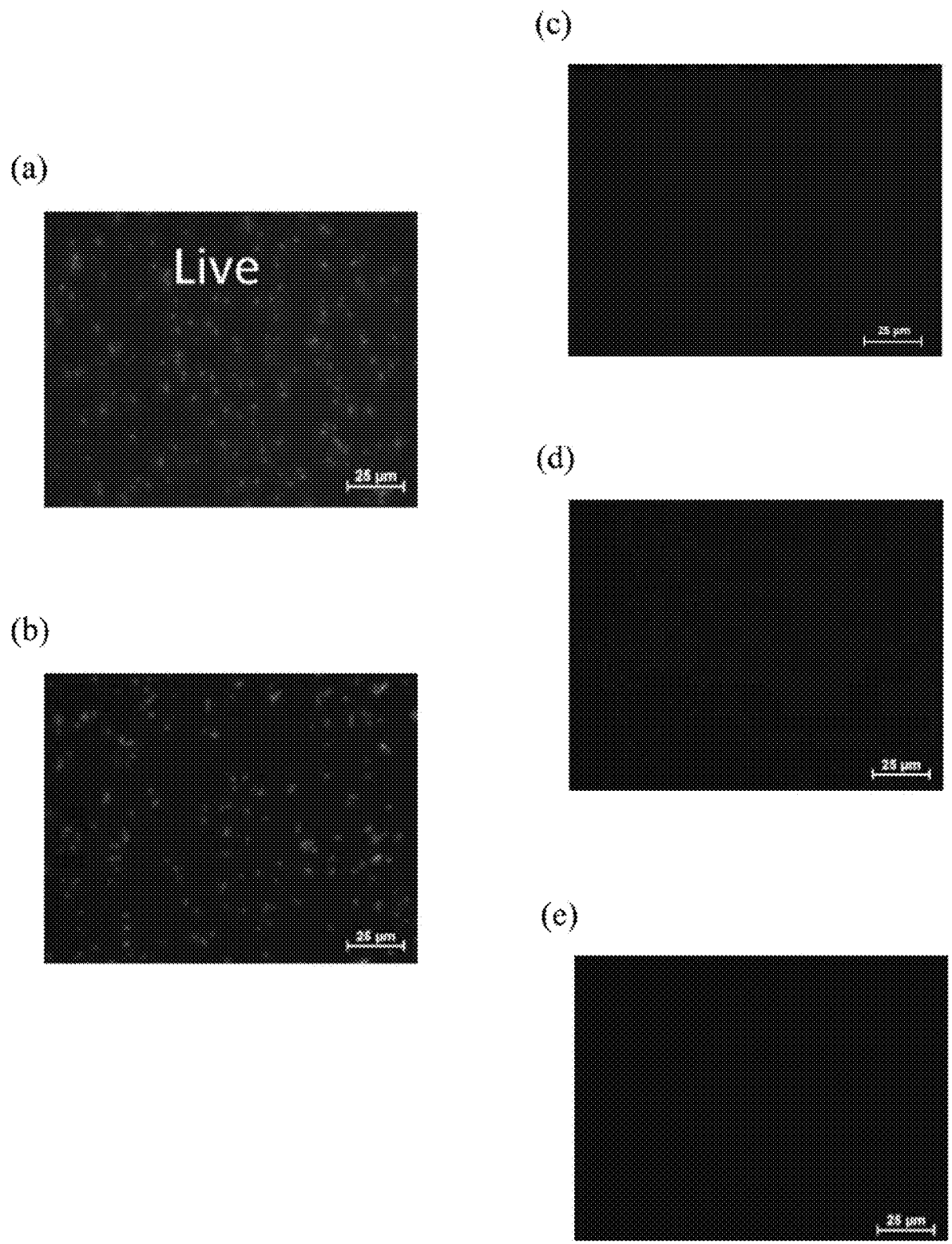
FIG. 8 is fluorescent staining results of antibiotic susceptibility testing using the microfluidic chip of FIG. 1.

As to the determination of the minimum inhibitory concentration, a quantitative dye can be added into each of the first reaction chamber 122, the second reaction chamber 124a, the second reaction chamber 124b, the second reaction chamber 124c, and the second reaction chamber 124d as mentioned above. After few minutes, an upright fluorescent microscope is applied for determining fluorescent staining results as shown in FIG. 8. In details, the fluorescent staining results of the first mixing solution and each of the second mixing solutions (that is, the concentration of the antibiotic solution is 0 µg/mL, 2 µg/mL, 4 µg/mL, 6 µg/mL and 8 µg/mL, respectively) are shown, separately, from FIG. 8 (*a*) to FIG. 8 (*e*). Live bacteria will show green fluorescence, and there is almost no live bacteria when the concentration of the antibiotic solution is 4 µg/mL as shown in FIG. 8 (*c*). That is, the antibiotic solution, which contains vancomycin, for the standard strain *Enterococcus* 29212 has the minimum inhibitory concentration of 4 µg/mL. Moreover, the standard strain *Enterococcus* 29212 is determined to be susceptible to the vancomycin-containing solution according to the CLSI guidelines. The incubation time and the determined minimum inhibitory concentration of the standard strain *Enterococcus* 29212 in Test 1 are listed in Table 1.

The determination of the minimum inhibitory concentration performed by the microfluidic system provided in the present disclosure obtains the same result as the determination of the minimum inhibitory concentration performed by the commercially available E-Test® kit. Thus, the accuracy of the present disclosure is further proved.

Alternatively, a proper pH indicator, such as phenol red, also can be added to the broth as a determination method. In details, a pH-dependent colorimetric broth, which includes brain heart infusion (BHI) media supplemented with 1% glucose and 0.05% phenol red, and antibiotics, are loaded. Then, the standard strain *Enterococcus* 29212 is loaded as the bacteria suspension to be tested herein for the antibiotic susceptibility testing. Please refer to FIG. 9, which is colorimetric results of the antibiotic susceptibility testing of the standard strain *Enterococcus* 29212 diluted by the microfluidic chip of FIG. 1. In particular, incubation times from FIG. 9(*a*) to FIG. 9(*f*) are 0 hour, 4 hours, 10 hours, 20 hours, 23 hours, and 24 hours.

Figure 9:
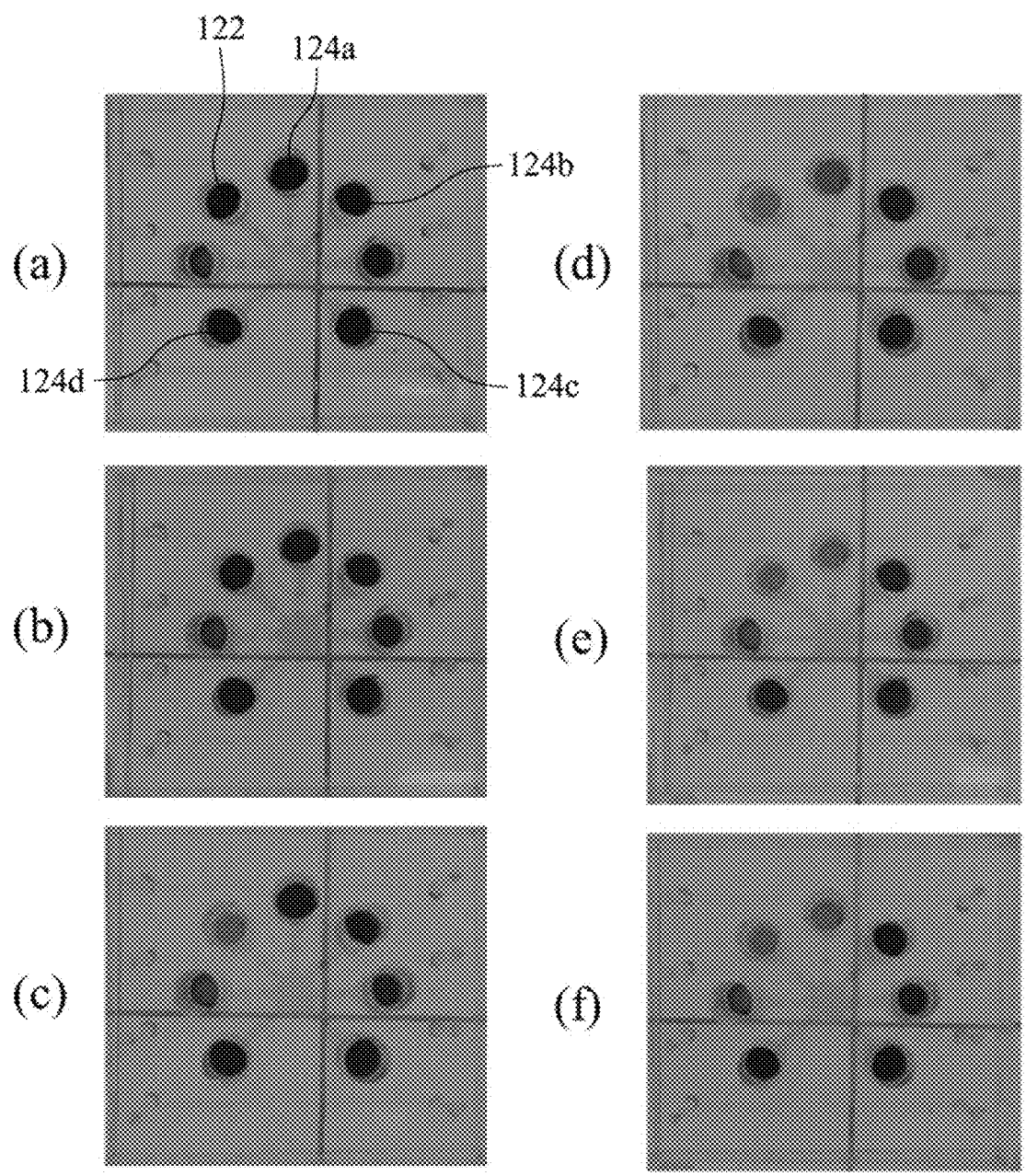
FIG. 9 is colorimetric results of an antibiotic susceptibility testing of standard strain *Enterococcus* (ATCC 29212) diluted by the microfluidic chip of FIG. 1.

The pH-dependent colorimetric broth will be transformed into an acidic pH due to bacterial growth, and the phenol red can be visually observed through color change from red to yellow. As shown in FIG. 9(*c*), the first mixing solution of the first reaction chamber 122, which is designed as the control group (that is, the concentration of vancomycin in the first mixing solution is 0 µg/mL), can be visually observed through color change from red to yellow after 10 hours of incubation. After 20 hours of incubation as shown in FIG. 9(*d*), the second mixing solution of the second reaction chamber 124a (that is, the concentration of vancomycin in the second mixing solution is 2 µg/mL) also can be visually observed through color change from red to yellow. After 24 hours of incubation as shown in FIG. 9(*f*), no color changes are observed in the second solutions of the second reaction chamber 124b, the second reaction chamber 124c and the second reaction chamber 124d (that is, the concentrations of vancomycin in the second mixing solutions are 4 µg/mL, 6 µg/mL and 8 µg/mL, respectively). That is, there is no bacteria growth in each of the second reaction chamber 124b, the second reaction chamber 124c and the second reaction chamber 124d. Therefore, the results of the antibiotic susceptibility testing can be visually observed that the bacteria standard strain *Enterococcus* 29212 is susceptible to vancomycin and the minimum inhibitory concentration is determined to be 4 µg/mL after 20 hours of incubation by the microfluidic system of the present disclosure.

Accordingly, the microfluidic system can obtain the same result as the conventional method without complicated manual operations and the need for professional training. Furthermore, the antibiotic solution can be loaded, diluted and mixed on the microfluidic chip automatically, and the results can be visually observed so that the abovementioned microfluidic system is sufficient to replace the conventional method.

Test 2

In Test 2, the antibiotic solution, the dilution mode and the operation of the microfluidic system are the as Test 1. However, a bacterial suspension to be tested of Test 2 is the bacterial suspension containing *E. faecium* (vancomycin-resistant *Enterococcus*). In particular, a genotype of the vancomycin-resistant *Enterococcus* in Test 2 is vanA, and a minimum inhibitory concentration thereof is determined by the conventional method (E-Test®) to be 32 µg/mL. The incubation time and the determined minimum inhibitory concentration of *E. faecium* (vanA) in Test 2 are listed in Table 1.

Test 3

In Test 3, the antibiotic solution, the dilution mode and the operation of the microfluidic system are the as Test 1. However, a bacterial suspension to be tested of Test 3 is the bacterial suspension containing *E. faecium* (vancomycin-resistant *Enterococcus*). In particular, a genotype of the vancomycin-resistant *Enterococcus* in Test 3 is vanB, and a minimum inhibitory concentration thereof is determined by the conventional method (E-Test®) to be 8 µg/mL. The incubation time and the determined minimum inhibitory concentration of *E. faecium* (vanB) in Test 3 are listed in Table 1.

Test 4

In Test 4, the antibiotic solution, the dilution mode and the operation of the microfluidic system are the as Test 1. However, a bacterial suspension to be tested of Test 4 is the bacterial suspension containing *E. gallinarum* (vancomycin-resistant *Enterococcus*). In particular, a genotype of the vancomycin-resistant *Enterococcus* in Test 4 is vanC1, and a minimum inhibitory concentration thereof is determined by the conventional method (E-Test®) to be 3 µg/mL. The incubation time and the determined minimum inhibitory concentration of *E. gallinarum* (vanC1) in Test 4 are listed in Table 1.

Test 5

In Test 5, the antibiotic solution, the dilution mode and the operation of the microfluidic system are the as Test 1. However, a bacterial suspension to be tested of Test 5 is the bacterial suspension containing *E. casseliflavus* (vancomycin-resistant *Enterococcus*). In particular, a genotype of the vancomycin-resistant *Enterococcus* in Test 4 is vanC2, and a minimum inhibitory concentration thereof is determined by the conventional method (E-Test®) to be 4 µg/mL. The incubation time and the determined minimum inhibitory concentration of *E. casseliflavus* (vanC2) in Test 5 are listed in Table 1.

TABLE 1

| Bacteria | E-test ® | | Microfluidic system of Embodiment 1 | |
|---|---|---|---|---|
| | MIC (µg/mL) | Incubation time (hours) | MIC (µg/mL) | Incubation time (hours) |
| Test 1 | 4 | 24 | 4 ± 0 | 20 |
| Test 2 | 32 | 24 | >16 ± 0 | 24 |
| Test 3 | 8 | 24 | 4 ± 0 | 19 |
| Test 4 | 3 | 24 | 4 ± 0 | 16 |
| Test 5 | 4 | 24 | 6 ± 0 | 17 |

As shown in Table 1, the date obtained by the microfluidic system and the conventional method (E-Test®) for both standard strain and clinical VREs are within an acceptable margin of error according to CLSI guidelines. However, the incubation of the microfluidic system of the present disclosure can be carried out from 16 hours to 24 hours, that is, the testing using the microfluidic system is quicker than the conventional method.

Test 6

In Test 6, vancomycin-intermediate *Staphylococcus aureus* (VISA) is designed as a bacterial suspension to be tested, and two antibiotic solutions, that is, vancomycin and ceftazidime, with different concentrations are prepared. In details, the two antibiotic solutions are transported, separately, to each of the second reaction chambers 124a', 124b', 124c', 124d', 124e', 124f', 124g', 124h', 124i', 124j', 124k' to mix with the broth and the bacterial suspension to be tested. Then, concentrations of vancomycin of the second reaction chambers 124a', 124b', 124c', 124d', 124e', 124f', 124g', 124h', 124i', 124j', 124k' are 4 µg/mL, 6 µg/mL, 4 µg/mL, 4 µg/mL, 4 µg/mL, 0 µg/mL, 6 µg/mL, 6 µg/mL, 2 µg/mL, 2 µg/mL and 2 µg/mL, respectively. Furthermore, concentrations of ceftazidime of the second reaction chambers 124a', 124b', 124c', 124d', 124e', 124f', 124g', 124h', 124i', 124j', 124k' are 2 µg/mL, 2 µg/mL, 4 µg/mL, 6 µg/mL, 0 µg/mL, 4 µg/mL, 6 µg/mL, 4 µg/mL, 6 µg/mL, 4 µg/mL and 2 µg/mL, respectively. In addition, a proper pH indicator, such as phenol red, is added to the broth in Test 6. After incubation at 37° C. for 24 hours, results can be visually observed.

Figure 10:
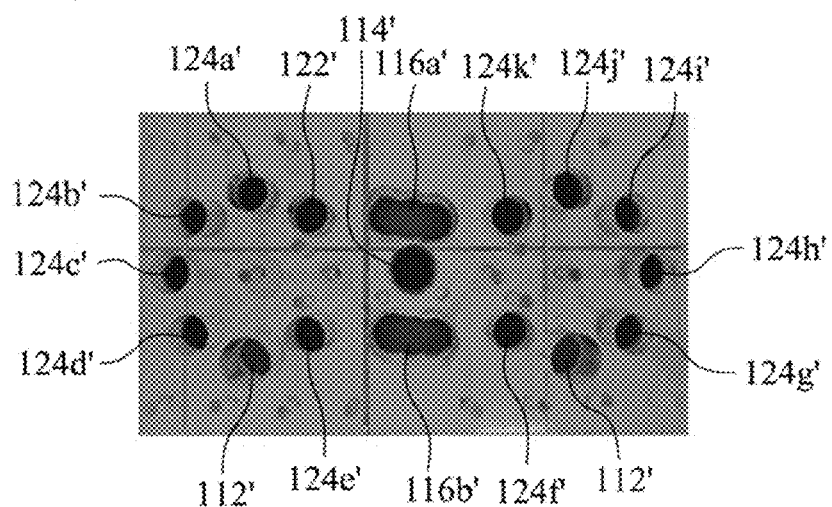
FIG. 10 is colorimetric results of an antibiotic susceptibility testing of clinical bacteria against concentrations of vancomycin and ceftazidime diluted by the microfluidic chip of FIG. 6.
Figure 10:
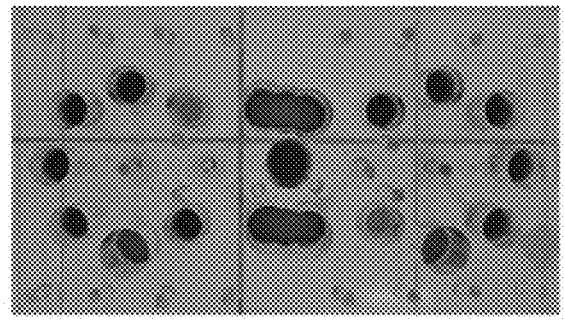
Figure 10:
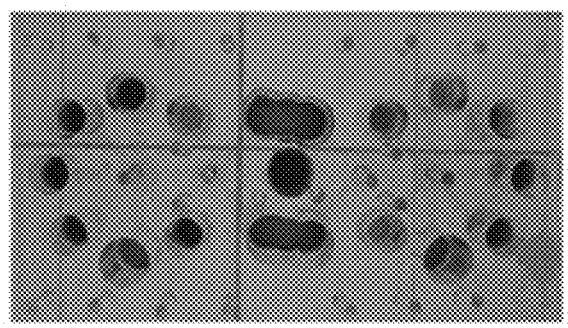
Figure 10:
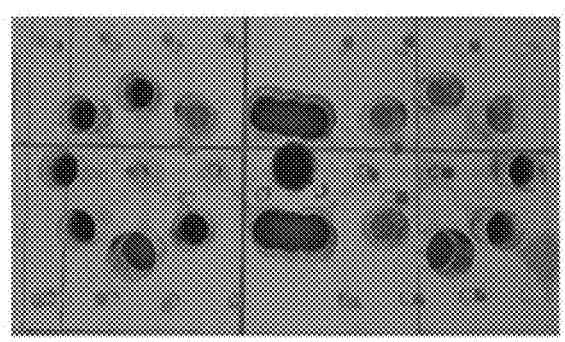

Please refer to FIG. 10, which is colorimetric results of an antibiotic susceptibility testing of clinical bacteria against concentrations of vancomycin and ceftazidime diluted by the microfluidic chip of FIG. 6. In particular, incubation times from FIG. 10(*a*) to FIG. 10(*d*) are 0 hour, 10 hours, 17 hours and 24 hours. As shown in FIG. 10(*b*), the first mixing solution of the first reaction chamber 122', which is designed as the control group (the concentrations of vancomycin and ceftazidime therein are 0 µg/mL), can be visually observed through color change from red to yellow after 10 hours of incubation. In addition, the second mixing solution loaded in the second reaction chamber 124' (the concentrations of vancomycin and ceftazidime therein are 0 µg/mL and 4 µg/mL, separately) also can be visually observed through color change from red to yellow after 10 hours of incubation. After 24 hours of incubation as shown in FIG. 10(*d*), slight color changes are observed in each of the second reaction chambers 124a', 124b', 124c', 124d', 124e', 124g', 124h'. However, the abovementioned color changes are not obvious compared to color changes in each of the first reaction chamber 122' and the second reaction chambers 124', 124i', 124j', 124k'. That is, the bacteria growth within the second reaction chambers 124a', 124b', 124c', 124d', 124e', 124g', 124h' are inhibited by vancomycin and ceftazidime.

Minimum inhibitory concentrations of vancomycin and ceftazidime for the vancomycin-intermediate *Staphylococcus aureus* can be visually observed to be 4 µg/mL and 2 µg/mL after 24 hours of incubation by the microfluidic system of Embodiment 2 of the present disclosure. Then, a fractional inhibitory concentration index of the two antibiotic solutions for the vancomycin-intermediate *Staphylococcus aureus* can be derived from the following equation: $FIC_{index}=FIC_A+FIC_B$. $FIC_A$ is calculated as a quotient between the minimum inhibitory concentration of vancomycin in combination and the minimum inhibitory concentration of vancomycin alone, and $FIC_B$ is calculated as a quotient between the minimum inhibitory concentration of ceftazidime in combination and the minimum inhibitory concentration of ceftazidime alone. In particular, the combination can be determined as synergic when the fractional inhibitory concentration index is ≤0.5, as antagonistic when the fractional inhibitory concentration index is >4. The results between synergy and antagonistic tendency are defined as additive or indifferent. Thus, the combination was considered to exhibit an indifferent effect because the fractional inhibitory concentration index is calculated to be 4/3 (that is, 4/3+2/>256≈4/3) by observing the pH shift-induced color change.

Accordingly, Test 6 further proves that the microfluidic system can omit complicated manual operations and the need for professional training. Furthermore, the antibiotic solution can be loaded, diluted and mixed on the microfluidic chip automatically, and the results can be visually observed so that the abovementioned microfluidic system is sufficient to replace the conventional method.

To sum up, the manual operation of the conventional method, such as the distribution and dilution of the bacteria suspension and the antibiotic solution, can be performed automatically by the microfluidic system of the present disclosure. The transportation and mixing of the liquid can be preciously and efficiently performed through the integration of the pneumatic micro-pumping unit and the pneumatic micro-valves for avoiding the sample cross-contamination. In addition, the antibiotic susceptibility testing performed by the abovementioned microfluidic system is quicker than the conventional method and does not need any expensive device and professional determination. Thus, a rapid screening can be achieved, and labor costs can be reduced.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An automatic microfluidic system for antibiotic susceptibility testing, at least comprising:
   a microfluidic chip, comprising:
      a fluid storage unit comprising:
         a first fluid storage chamber for storing a bacterial suspension;
         a second fluid storage chamber for storing a broth, wherein the broth comprises a pH indicator, and a pH range for color change of the pH indicator is ranged from pH 6.0 to pH 8.0; and
         a third fluid storage chamber for storing an antibiotic solution;
      a reaction unit comprising a first reaction chamber and at least two second reaction chambers;
      a pneumatic micropump adjacently disposed to the fluid storage unit and the reaction unit, wherein the pneumatic micropump comprises an air inlet hole, the air inlet hole is located on an upper central portion of the pneumatic micropump, and the pneumatic micropump is applied for repeatedly and quantitatively transporting the broth and the bacterial suspension to the first reaction chamber to form a first mixing solution and for repeatedly and quantitatively transporting the broth, the bacterial suspension and the antibiotic solution to the second reaction chambers to form at least two second mixing solutions; and
      a plurality of valve units comprising:
         a plurality of pneumatic micro-valves disposed between the fluid storage unit and the pneumatic micropump, and between the pneumatic micropump and the reaction unit; and
         a plurality of valve control air holes for controlling the opening and closing of the pneumatic micro-valves, wherein each of the valve control air holes is correspondingly connected to one of the pneumatic micro-valves;
      wherein the pneumatic micropump comprises at least one first pneumatic micropump and at least one second pneumatic micropump communicated with each other, and the fluid storage unit and the reaction unit of the microfluidic chip are radially distributed around the pneumatic micropump.

2. The automatic microfluidic system for antibiotic susceptibility testing of claim 1, wherein the fluid storage unit comprises at least two third fluid storage chambers, one of the third fluid storage chambers is for storing the antibiotic solution, and the other one of the third fluid storage chambers is for storing the other antibiotic solution.

3. The automatic microfluidic system for antibiotic susceptibility testing of claim 1, wherein the microfluidic chip is composed of a substrate, a first flexible material layer disposed on the substrate and a second flexible material layer disposed on the first flexible material layer, and the substrate, the first flexible material layer and the second flexible material layer are configured for defining the fluid storage unit, the reaction unit, the pneumatic micropump and the pneumatic micro-valves.

4. The automatic microfluidic system for antibiotic susceptibility testing of claim 3, wherein the first material layer and the second flexible material layer are made of poly (dimethylsiloxane).

5. The automatic microfluidic system for antibiotic susceptibility testing of claim 3, wherein the substrate is made of glass.

6. The automatic microfluidic system for antibiotic susceptibility testing of claim 1, wherein the pneumatic micro-valves are normally-closed micro-valves.

7. The automatic microfluidic system for antibiotic susceptibility testing of claim 1, further comprising:
   a temperature control apparatus for controlling a temperature of the microfluidic chip.

8. The automatic microfluidic system for antibiotic susceptibility testing of claim 7, wherein the temperature control apparatus is a thermos plate disposed under the microfluidic chip.

9. The automatic microfluidic system for antibiotic susceptibility testing of claim 7, wherein the temperature control apparatus is an incubator for containing the microfluidic chip.

10. The automatic microfluidic system for antibiotic susceptibility testing of claim 1, further comprising:
    an absorbance detection device for detecting an optical density of the first mixing solution and an optical density of each of the second mixing solutions, after an incubation time.

11. A method for operating the automatic microfluidic system for antibiotic susceptibility testing of claim 1, comprising:

performing a first transportation step for transporting the bacterial suspension to each of the first reaction chamber and the second reaction chambers by the pneumatic micropump;

performing at least one second transportation step for transporting the broth to each of the first reaction chamber and the second reaction chambers by the pneumatic micropump;

performing at least one third transportation step for transporting the antibiotic solution to at least one of the second reaction chambers by the pneumatic micropump, wherein a concentration of the antibiotic solution in each of the second mixing solutions is adjusted by a frequency of transporting the antibiotic solution and the broth to the second reaction chamber;

performing an incubation step, wherein the first mixing solution and the second mixing solutions are allowed to stand for an incubation time; and performing a determination step for determining a result of the antibiotic susceptibility testing.

12. The method of claim 11, further comprising:
repeating the second transportation step for obtaining a first ratio of a volume of the broth of the first reaction chamber to a volume of the broth of one of the second reaction chambers to a volume of the broth of the other of the second reaction chambers; and repeating the third transportation step for obtaining a second ratio of a volume of the antibiotic solution of the first reaction chamber to a volume of the antibiotic solution of one of the second reaction chambers to a volume of of the antibiotic solution of the other of the second reaction chambers;

wherein the first ratio is a1 to a2 to a3, the second ratio is b1 to b2 to b3, and the following condition is satisfied:

$$(a1+b1)=(a2+b2)=(a3+b3).$$

13. The method of claim 11, after the first transportation step, further comprising:
performing a cleaning step for transporting the broth to the pneumatic micropump to clean the pneumatic micropump; and perform a waste liquid recycling step for recycling the broth to the first fluid storage chamber.

14. The method of claim 11, after any one of the first transportation step, the second transportation step and the third transportation step, further comprising:
performing a valve controlling step for applying a suction force and a push force through the valve control air holes for opening or closing the pneumatic microvalves corresponding to the valve control air holes.

15. The method of claim 14, wherein a gauge pressure of the suction force is larger than or equal to 10 kPa and smaller than or equal to 80 kPa, and a gauge pressure of the push force is larger than or equal to 6 kPa and smaller than or equal to 140 kPa.

16. The method of claim 11, wherein a temperature of the microfluidic chip is controlled during the incubation step.

17. The method of claim 11, wherein the determination step comprises:
adding a dye into the first mixing solution and each of the second mixing solutions; and performing a fluorescence detection step for determining a minimum concentration without live bacteria of the second mixing solutions.

18. The method of claim 11, wherein the broth comprises a pH indicator and the determination step comprises:
determining a minimum concentration without color change of the second mixing solutions.

19. The method of claim 11, wherein the determination step comprises:
performing an absorbance detection step for detecting an optical density of the first mixing solution and an optical density of each of the second mixing solutions so as to determine bacterial concentrations of the second mixing solutions.

20. The method of claim 11, wherein the incubation time of the incubation step is larger than or equal to 16 hours and less than or equal to 24 hours.

21. A method for operating the automatic microfluidic system for antibiotic susceptibility testing of claim 2, comprising:
performing a first transportation step for transporting the bacterial suspension to the first reaction chamber and each of the second reaction chambers by the pneumatic micropump;

performing at least one second transportation step for transporting the broth to the first reaction chamber and each of the second reaction chambers by the pneumatic micropump;

performing at least one third transportation step for transporting the antibiotic solution and the other antibiotic solution to at least one of the second reaction chambers by the pneumatic micropump, wherein concentrations of the antibiotic solution and the other antibiotic solution in each of the second mixing solutions is adjusted by a frequency of transporting the antibiotic solution, the other antibiotic solution and the broth to each of the second reaction chambers;

performing an incubation step, wherein the first mixing solution and the second mixing solutions are allowed to stand for an incubation time; and performing a determination step for determining a result of the antibiotic susceptibility testing.

22. The method of claim 21, after any one of the first transportation step, the second transportation step and the third transportation step, further comprising:
performing a valve controlling step for applying a suction force and a push force through the valve control air holes for opening and closing the pneumatic microvalves corresponding to the valve control air holes.

23. The method of claim 22, wherein a gauge pressure of the suction force is larger than or equal to 10 kPa and smaller than or equal to 80 kPa, and a gauge pressure of the push force is larger than or equal to 6 kPa and smaller than or equal to 140 kPa.

24. The method of claim 21, wherein the broth comprises a pH indicator and the determination step comprises:
determining a minimum concentration without color change of the second mixing solutions.

* * * * *